United States Patent
Van Den Hombergh et al.

(10) Patent No.: US 7,759,102 B2
(45) Date of Patent: Jul. 20, 2010

(54) TALAROMYCES XYLANASES

(75) Inventors: Johannes Petrus Theodorus Wilhelmus Van Den Hombergh, De Meern (NL); Jan-Metske Van Der Laan, Breda (NL); Jean-Marc Georges Daran, Naaldwijk (NL)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 12/142,852

(22) Filed: Jun. 20, 2008

(65) Prior Publication Data

US 2008/0274886 A1    Nov. 6, 2008

Related U.S. Application Data

(62) Division of application No. 10/381,328, filed as application No. PCT/EP00/09257 on Sep. 21, 2000.

(51) Int. Cl.
C12N 9/24 (2006.01)
C12N 15/00 (2006.01)
C12N 1/20 (2006.01)
C12N 1/00 (2006.01)
C12Q 1/68 (2006.01)
C12P 21/06 (2006.01)
C07H 21/04 (2006.01)
A02H 5/00 (2006.01)

(52) U.S. Cl. .......................... 435/200; 435/6; 435/69.1; 435/320.1; 435/252.3; 435/254.3; 435/254.6; 435/484; 536/23.2; 800/298; 800/300

(58) Field of Classification Search .................. None
See application file for complete search history.

(56) References Cited

U.S. PATENT DOCUMENTS

| | | | |
|---|---|---|---|
| 4,683,202 A | 7/1987 | Mullis | |
| 5,358,864 A | 10/1994 | van den Broeck et al. | |
| 5,610,046 A | 3/1997 | van Ooyen et al. | |
| 5,610,048 A | 3/1997 | Schulein et al. | |
| 5,693,518 A | 12/1997 | Kofod et al. | |
| 5,876,988 A | 3/1999 | Selten et al. | |
| 5,885,819 A | 3/1999 | Kofod et al. | |
| 6,080,567 A | 6/2000 | Kofod et al. | |
| 6,197,564 B1 | 3/2001 | Kofod et al. | |
| 6,228,630 B1 | 5/2001 | Kofod et al. | |
| 6,432,672 B1 | 8/2002 | Selten et al. | |
| 6,586,209 B1 | 7/2003 | van Gorcom et al. | |
| 7,220,542 B2 | 5/2007 | van den Brink et al. | |
| 2004/0241647 A1 | 12/2004 | van den Brink et al. | |

FOREIGN PATENT DOCUMENTS

| EP | 0 096 340 A2 | 12/1983 |
|---|---|---|
| EP | 0 134 048 A1 | 3/1985 |
| EP | 0 184 433 A2 | 6/1986 |
| EP | 0 253 455 A1 | 1/1988 |
| EP | 0 284 603 | 10/1988 |
| EP | 0 301 670 A1 | 2/1989 |
| EP | 0 449 375 A2 | 10/1991 |
| EP | 0 463 706 A1 | 1/1992 |
| EP | 0 635 574 A1 | 1/1995 |
| WO | WO-91/19782 A1 | 12/1991 |
| WO | WO-92/01793 A1 | 2/1992 |
| WO | WO-92/17573 A1 | 10/1992 |
| WO | WO-94/21785 A1 | 9/1994 |
| WO | WO-98/04726 A1 | 2/1998 |
| WO | WO-98/30707 A2 | 7/1998 |
| WO | WO-98/46772 A2 | 10/1998 |
| WO | WO-99/32617 A2 | 7/1999 |
| WO | WO-01/42433 A2 | 6/2001 |

OTHER PUBLICATIONS

Whisstock et al. Quaterly Reviews of Biophysics, 2003, "Prediction of protein function from protein sequence and structure", 36(3): 307-340.*
Chica et al. Semi-rational approaches to engineering enzyme activity: combining the benefits of directed evolution and rational design, Curr Opin Biotechnol. Aug. 2005;16(4):378-84. Review.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Lejeune, International Search Report for PCT/EP00/09257.
International Preliminary Examination Report for PCT/EP00/09257.
Morales, P., et al., "Purification and Characterization of Alkaline Xylanases from *Bacillus polymyxa*", Appl. and Environmental Microbiology, vol. 59, No. 5, (1993), pp. 1376-1382.
Saraswat, V., et al., "Purification, Characterization and Substrate Specificities of Xylanase Isoenzymes from *Melanocarpus albomyces* IIS 68", Biosci. Biotechnol. Biochem, vol. 64, No. 6, (2000), pp. 1173-1180.
Aleksenko, A., et al., "Autonomous Plasmid Replication in *Aspergillus nidulans*: AMA1 and MATE Elements", Fungal Genetics and Biology, vol. 21, (1997), pp. 373-387.
Altschul, S.F., et al., "Basic Local Alighment Search Tool", J. Mol. Biol., vol. 215, (1990), pp. 403-410.
Altschul, S.F., "A Protein Alignment Scoring System Sensitive at All Evolutionary Distances", J. Mol. Evol., vol. 36, (1993), pp. 290-300.
Cunningham, B.C., et al., "High-Resolution Epitope Mapping of hGH-Receptor Interactions by Alanine-Scanning Mutagenesis", Science, vol. 244, (1989), pp. 1081-1085.
Davies, R.W., "Heterologous Gene Expression and Protein Secretion in *Aspergillus*", Progress in Industrial Microbiology, vol. 29, (1994), pp. 527-560.

(Continued)

Primary Examiner—Richard Hutson
Assistant Examiner—Iqbal H Chowdhury
(74) Attorney, Agent, or Firm—Connolly Bove Lodge & Hutz LLP

(57) ABSTRACT

Novel polypeptides possessing (endo)xylanase activity are disclosed which can degrade cellulose implant extracts and plant materials. The polypeptides can cleave β-D-xylan polymers at internal (1-4) bonds between adjacent xylopyranosyl units. The amino acid sequence and encoding DNA sequence is given and the polypeptide was used to treat cellulose in the preparation of edible foodstuffs and animal feed. The polypeptides have both arabinoxylanase and xylosidase activity.

12 Claims, No Drawings

OTHER PUBLICATIONS

Devereux, J., et al., "A Comprehensive Set of Sequence Analysis Programs for the VAX", Nucleic Acids Research, vol. 12, (1984), pp. 387-395.

de Vos, A. M., et al., "Human Growth Hormone and Extracellular Domain of Its Receptor: Crystal Structure of the Complex", Science, vol. 255, (1992), pp. 306-312.

Ford, C.F., et al., "Fusion Tails for the Recovery and Purification of Recombinant Proteins", Protein Expression and Purification, vol. 2, (1991), pp. 95-107.

Henikoff, S. et al., "Amino Acid Substitution Matrices from Protein Blocks", Proc. Natl. Acad. Sci USA, vol. 89, (1992), pp. 10915-10919.

Karlin, S., et al., "Applications and Statistics for Multiple High-scoring Segments in Molecular Sequences", Proc. Natl. Acad. Sci. USA, vol. 90, (1993), pp. 5873-5877.

Lever, M., et al., "A Comparison of 4-hydroxybenzoic Acid Hydrazide (PAHBAH) with other Reagents for the Determination of Glucose", J. Lab. Clin. Med., vol. 82, (1973), pp. 649-655.

Raper, K.B., et al., "The Genus *Aspergillus*", The Williams & Wilkins Co., Baltimore, (1965), pp. 293-344.

Romanos, M.A., et al., "Foreign Gene Expression in Yeast: a Review", Yeast, vol. 8, (1992), pp. 423-488.

Saiki, R.K., et al., "Primer-directed Enzymatic Amplification of DNA with a Thermostable DNA Polymerase", Science, vol. 239, (1988), pp. 487-491.

Smith, L.J., et al., "Human Interleukin 4, The Solution Structure of a Four-helix Bundle Protein", J. Mol. Biol., vol. 224, (1992), pp. 899-904.

Tuohy, M.G., et al., "The Xylan-degrading Enzyme System of *Talaromyces emersonii*: Novel Enzymes with Activity Against aryl β-D-Xylosides and Unsubstituted Xylans", Biochem. J., vol. 290, (1993), pp. 515-523.

Tuohy, M.G., et al., "Characterization of the Individual Components of the Xylanolytic Enzyme System of *Talaromyces emersonii*", Bioresource Tech., vol. 50, (1994), pp. 37-42.

van Zeijl, C.M.J., et al., "An Improved Colony-PCR Method for Filamentous Fungi for Amplication of PCT-fragments of Several Kilobases", J. of Biotechnol., vol. 59, (1998), pp. 221-224.

Wlodaver, A., et al., "Crystal Structure of Human Recombinant Interleukin-4 at 2.25 Å Resolution", FEBS, vol. 309, No. 1, (1992), pp. 59-64.

\* cited by examiner

TALAROMYCES XYLANASES

RELATED APPLICATIONS

This application is a divisional of copending U.S. application Ser. No. 10/381,328 filed Mar. 21, 2003, which is the National Stage Application PCT/EP00/09257 filed Sep. 21, 2000. The entire content of each above-mentioned application is hereby incorporated by reference in entirety.

FIELD OF INVENTION

The present invention relates to a novel xylanases, such as those from *Talaromyces* xylanases and their use in degrading xylan in cellulose. The xylanases find use in baking, in animal feed (to improve feed conversion) and in paper production.

BACKGROUND OF THE INVENTION

The composition of a plant cell wall is complex and variable and contains several carbohydrate biopolymers. Polysaccharides are mainly found in the form of long chains of cellulose (the main structural component of the plant cell wall), hemicellulose (comprising various B-xylan chains, such as xyloglucans) pectin and lignin. The most abundanthemicelluloses are xylans and their derivatives such as arabinoxylan and xyloglycan.

Plant hemicelluloses include xylan, arabinoxylan, glucuronoarabinoxylan and xyloglucan. Xylan (CAS Registry No. 9014-63-5) consists of a backboneouf β-1,4-linked D-xylopyranosyl units, optionally substituted with side chains such as arabinose and/or glucuronic acid residues. The structure is:

→4)-β-D-Xylp-(1→4)-β-D-Xylp(2←1A)-(1→4)-
ss-D-Xylp-(1→4)-β-D-Xylp(3←1B)-(1→

(Xylp=xylopyranosyl unit; A=α-(4-0)-methyl-(D-glucuronopyranosyl) unit, sometime an acetyl; and B=α-(L-arabinofuranosyl) unit, sometimes an acetyl).

Xylans may represent more than 30% of the dry weight of terrestrial plants. Hence xylan is an important component of materials from natural sources that are used in industrial processes ranging from baking, improvement of animal feed conversion and paper production.

Basic differences exist between monocotyledons (e.g. cereals and grasses) and dicotyledons (e.g. clover, rapeseed and soybean) and between the seed and vegetative parts of the plant. Monocotyledons are characterized by the presence of an arabinoxylan complex as the major hemicellulose backbone, and the main structure of hemicellulose in dicotyledons is a xyloglucan complex. Higher pectin concentrations are found in dicotyledons than in monocotyledons. Seeds are generally high in peptic substances but relatively low in cellulosic material.

Cellulose degrading enzymes are used for the processing of plant material in food as well as feed applications or as a food or feed additive due to of their capability to act on main plant cell wall substituents.

Most of the cellulose degrading enzymes available to the industry appear to be xylanases with a relatively low molecular weight and a moderate stability at higher temperatures. However, for certain applications it is desirable to use a xylanase with a relatively high thermostability. If a xylanase is to be used as an animal feed additive then a high thermostability is preferred because of the high temperature conditions applied during pelleting the animal feed.

SUMMARY OF THE INVENTION

A novel xylanase is now provided which is able to cleave β-D-xylan such as present in plant material. The xylanase may also be able to hydrolyse arabinoxylan (or have arabinoxylanase activity) and anaryl-β-D-xylopyranoside (or have xylosidase activity).

Accordingly, the present invention provides an (isolated) β-xylanase polypeptide comprising:

(i) the amino acid sequence of SEQ ID No: 2; or (ii) a variant of (i) which is capable of cleaving β-D-xylan; or (iii) a fragment of (i) or (ii) which is capable of cleavings β-D-xylan.

According to another aspect of the invention there is provided a polynucleotide which comprises:

(a) the nucleic acid sequence of SEQ ID No. 1 or, a sequence encoding a polypeptide of the invention;

(b) a sequence which is complementary to, or which hybridises to, a sequence as defined in (a);

(c) a fragment of a sequence in (a) or (b);

(d) a sequence having at least 60% identity to a sequence as defined in (a), (b) or (c);

or (e) a sequence that is degenerate as a result of the genetic code to any of the sequences as defined in (a) to (d).

The invention also provides:

an (e.g. expression) vector which comprises a polynucleotide of the invention and which may be capable of expressing a polypeptide of the invention;

a cell line comprising a vector of the invention;

a method of producing a polypeptide of the invention which method comprises maintaining a cell line of the invention under conditions suitable for obtaining expression of the polypeptide and, if necessary, isolating the polypeptide;

a method of degrading β-D-xylan, the method comprising contacting a material comprising β-D-xylan with a polypeptide of the invention; and a method for identification of a compound that modulates xylanase activity, which method comprises contacting a polypeptide of the invention with a test compound in the presence of β-D-xylan and monitoring for or detecting any modulation of activity.

BRIEF DESCRIPTION OF THE SEQUENCES

SEQ ID No. 1 is a DNA sequence encoding the xylanase of the invention from *Talaromyces emersonii*;

SEQ ID No. 2 is the amino acid sequence of the xylanase; and

SEQ ID Nos. 3 and 4 are artificial PCR primers that hybridize to SEQ ID No. 1.

DETAILED DESCRIPTION OF THE INVENTION

A. Polynucleotides

The present invention provides an (e.g. isolated and/or purified) polynucleotide encoding a polypeptide of the invention. The present invention thus provides a polynucleotide encoding a xylanase whose amino acid sequence is set out in SEQ ID No. 2 (such as the mature sequence from amino acids 23 to 408). The present invention further provides a polynucleotide encoding a polypeptide having substantial amino acid sequence homology to the amino acid sequence set out in SEQ ID No. 2. Also included is a polynucleotide selected from:

(a) a polynucleotide comprising the nucleotide sequence (for example, from polynucleotides 69 to 1224) set out in SEQ ID No. 1, or the complement thereof;

(b) a polynucleotide comprising a nucleotide sequence capable of (e.g. selectively) hybridising to a nucleotide sequence set out in SEQ ID No. 1, or a fragment thereof;

(c) a polynucleotide comprising a nucleotide sequence capable of (e.g. selectively) hybridising to the complement of the nucleotide sequence set out in SEQ ID No. 1, or a fragment thereof; and/or (d) a polynucleotide comprising a polynucleotide sequence that is degenerate as a result of the genetic code to a polynucleotide defined in (a), (b) or (c).

A polynucleotide of the invention also includes a polynucleotide which:

(a) encodes a polypeptide having xylanase activity, which polynucleotide is:

(1) the coding sequence of SEQ ID No. 1 (for example, from polynucleotides 69 to 1224);

(2) a sequence which hybridises selectively to the complement of sequence defined in (1); or (3) a sequence that is degenerate as a result of the genetic code with respect to a sequence defined in (1) or (2); or (b) is a sequence complementary to a polynucleotide defined in (a).

References to SEQ. ID. No. 1 can be substituted by the mature coding sequence (polynucleotides 69 to 1224) unless the text requires otherwise.

Hybridisable Sequences

The term "capable of hybridizing" means that the target polynucleotide of the invention can hybridize to the nucleic acid used as a probe (for example the nucleotide sequence set out in SEQ. ID No. 1, or a fragment thereof or the complement thereof) at a level significantly above background. The invention also includes nucleotide sequences that encode for the xylanase or variants thereof as well as nucleotide sequences which are complementary thereto. The nucleotide sequence may be RNA or DNA and thus includes genomic DNA, synthetic DNA or cDNA. Preferably the nucleotide sequence is a DNA sequence and most preferably, a cDNA sequence. Typically a polynucleotide of the invention comprises a contiguous sequence of nucleotides which is capable of hybridizing under selective conditions to the coding sequence or the complement of the (e.g. mature) coding sequence of SEQ ID No. 1. Such nucleotides can be synthesized according to methods well known in the art[1].

A polynucleotide of the invention can hybridize to the coding sequence or the complement of the (e.g. mature) coding sequence of SEQ ID No. 1 at a level significantly above background. Background hybridization may occur, for example, because of other cDNAs present in a cDNA library. The signal level (e.g. generated by the interaction between a polynucleotide of the invention and the coding sequence or complement of the coding sequence) is typically at least 10 fold, preferably at least 100 fold, as intense as interactions between other polynucleotides and the (e.g. mature) coding sequence of SEQ ID No. 1. The intensity of interaction may be measured, for example, by radiolabelling the probe, e.g. with $^{32}$P. Selective hybridization may typically be achieved using conditions of low stringency (0.3M sodium chloride and 0.03M sodium citrate at about 40° C.), medium stringency (for example, 0.3M sodium chloride and 0.03M sodium citrate at about 50° C.) or high stringency (for example, 0.3M sodium chloride and 0.03M sodium citrate at about 60°). Hybridization may be carried out under any suitable conditions known in the art[1] and, as a guide, low stringency can be 2×SSC at 55° C., medium stringency can be 0.5 to 0.1 or 0.2×SSC at 60° C. and high stringency can be 0.1 or 0.2×SSC at 60° C. or higher (erg. at 68° C.), all at 0.5% SDS.

Modifications

Polynucleotides of the invention may comprise DNA or RNA. They may be single or double stranded. They may also be polynucleotides which include within them one or more synthetic or modified nucleotides. A number of different types of modifications to polynucleotides are known in the art. These include methylphosphonate and phosphorothioate backbones and/or addition of acridine or polylysine chains at the 3' and/or 5' ends of the molecule. For the purposes of the present invention, it is to be understood that the polynucleotides described herein may be modified by any method available in the art.

It is to be understood that skilled persons may, using routine techniques, make nucleotide substitutions that do not affect the polypeptide sequence encoded by the polynucleotides of the invention to reflect the codon usage of any particular host organism, for example in which the polypeptides of the invention are to be expressed.

The (e.g. mature) coding sequence of SEQ ID No. 1 may be modified by nucleotide substitutions, for example from or up to 1, 2 or 3 to 10, 25, 50 or 100 substitutions. The polynucleotide may alternatively or additionally be modified by one or more insertions and/or deletions and/or by an extension at either or both ends. The modified polynucleotide generally encodes a polypeptide which has xylanase activity. Degenerate substitutions may be made and/or substitutions may be made which would result in a conservative amino acid substitution when the modified sequence is translated, for example as discussed with reference to polypeptides later.

Homologues

A nucleotide sequence which is capable of selectively hybridizing to (e.g. the complement of) the DNA coding sequence of SEQ ID No. 1 (or nucleotides 69-1224) may have at least 70%, at least 75%, at least 80%, at least 90%, at least 95%, at least 98% or at least 99% sequence identity (or homology) to the coding sequence of SEQ ID No. 1. This may be over a region of at least 20, preferably at least 30 or 60, for instance at least 100, at least 200, more preferably at least 300 contiguous nucleotides or optimally over the full length of SEQ ID No. 1.

Any combination of the above mentioned degrees of homology and minimum sized may be used to define polynucleotides of the invention, with the more stringent combinations (i.e. higher homology over longer lengths) being preferred. Thus for example a polynucleotide which is at least 80% or 90% homologous over 25, preferably over 30 nucleotides forms one aspect of the invention, as does a polynucleotide which is at least 90% homologous over 40 nucleotides.

Homologues of polynucleotide (or protein) sequences typically have at least 70% homology, preferably at least 80, 90%, 95%, 97% or 99% homology, for example over a region of at least 20, 25, 30, 100 more contiguous nucleotides (or amino acids). The homology may calculated on the basis of amino acid identity (sometimes referred to as "hard homology").

For example the UWGCG Package provides the BESTFIT program which can be used to calculate homology (for example used on its default settings5). The PILEUP and BLAST algorithms can be used to calculate homology or line up sequences (such as identifying equivalent or corresponding sequences, for example on their default settings[6, 7]).

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold[6,7]. These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

The BLAST program uses as defaults a word length (W) of 11 the BLOSUM62 scoring matrix[8] alignments (B) of 50, expectation (E) of 10, M=5, N=4, and a comparison of both strands.

The BLAST algorithm performs a statistical analysis of the similarity between two sequences[9]. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Primers and Probes

Polynucleotides of the invention include and may be used as a primer, e.g. a PCR primer, a primer for an alternative amplification reaction, a probe, or the polynucleotides may be cloned into vectors. Such primers, probes and other fragments will be at least or up to 20, 25, 30 or 40, for example at least 25, 30 or 40 nucleotides in length. They will typically be up to 30, 40, 50, 60, 70, 100, 150, 200 or 300 nucleotides in length, or this number (even up to as few nucleotides as 5 or 10 nucleotides) short of the (e.g. mature) coding sequence of SEQ ID No. 1.

In general, primers will be produced by synthetic means, involving a step-wise manufacture of the desired nucleic acid sequence one nucleotide at a time. Techniques for accomplishing this using automated techniques are readily available in the art. Examples of primers of the invention are set out in SEQ ID Nos 3 and 4.

Longer polynucleotides will generally be produced using recombinant means, for example using PCR (polymerase chain reaction) cloning techniques. This will involve making a pair of primers (e.g. of about 15-30 nucleotides) to a region of the xylanase which it is desired to clone, bringing the primers into contact with mRNA or cDNA obtained from a target (e.g. yeast, bacterial, plant, prokaryotic or fungal) cell, preferably of an *Talaromyces* strain, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the xylanase sequence described herein. Genomic clones corresponding to the cDNA of SEQ ID No. 1 or the xylanase gene containing, for example, introns and promoter regions are within the invention also and may also be obtained in an analogous manner (e.g. recombinant means, PCR, cloning techniques), starting with genomic DNA from a fungal, yeast, bacterial plant or prokaryotic cell.

The polynucleotides or primers may carry a revealing label, e.g. a radioactive or non-radioactive label. Suitable labels include radioisotopes such as $^{32}P$ or $^{35}S$, enzyme labels, or other protein labels such as biotin. Such labels may be added to polynucleotides or primers of the invention and may be detected using techniques known per se.

Polynucleotides, labelled or unlabelled may be used in nucleic acid-based tests for detecting or sequencing xylanase or a variant thereof in a (e.g. fungal) sample. Such tests for detecting generally comprise bringing a (e.g. fungal) sample (suspected of containing DNA into contact with a probe or primer of the invention under hybridizing conditions and detecting any duplex formed between the probe and nucleic acid in the sample. Such detection may be achieved using techniques such as PCR or by immobilizing the probe on a solid support, removing nucleic acid in the sample which is not hybridized to the probe, and then detecting nucleic acid which was hybridized to the probe. Alternatively, the sample nucleic acid may be immobilized on a solid support, and the amount of probe bound to such a support can be detected.

The probes of the invention may conveniently be packaged in the form of a test kit in a suitable container. In such kits the probe may be bound to a solid support where the assay format for which the kit is designed requires such binding. The kit may also contain suitable reagents for treating the sample to be probed, hybridizing the probe to nucleic acid in the sample, control reagents, instructions, and the like.

Preferably, the polynucleotide of the invention is obtainable from the same organism as the polypeptide, such as a fungus, in particular a fungus of the genus *Talaromyces*.

The polynucleotides of the invention also include variants of the sequence of SEQ ID No. 1 which have xylanase activity. Variants may be formed by additions, substitutions and/or deletions and may have the ability to cleave a β-D-xylan polymer.

Production of Polynucleotides

Polynucleotides which do not have 100% identity with (e.g. the mature coding sequence of) SEQ ID No. 1 but fall within the scope of the invention can be obtained in a number of ways. Thus variants of the xylanase sequence described herein may be obtained for example by probing genomic DNA libraries made from a range of organisms, for example those discussed as sources of the polypeptides of the invention. In addition, other fungal, plant or prokaryotic homologues of xylanase may be obtained and such homologues and fragments thereof in general will be capable of hybridising to SEQ ID No. 1. Such sequences may be obtained by probing cDNA libraries or genomic DNA libraries from other species, and probing such libraries with probes comprising all or part of SEQ ID. 1 under conditions of medium to high stringency (as described earlier). Nucleic acid probes comprising all or part of SEQ ID No. 1 may be used to probe cDNA libraries from other species, such as those described as sources for the polypeptides of the invention.

Species homologues may also be obtained using degenerate PCR which will use primers designed to target sequences within the variants and homologues encoding conserved amino acid sequences. The primers can contain one or more degenerate positions and will be used at stringency conditions lower than those used for cloning sequences with single sequence primers against known sequences.

Alternatively, such polynucleotides may be obtained by site directed mutagenesis of the xylanase sequences or variants thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The invention includes double stranded polynucleotides comprising a polynucleotide of the invention and its complement.

The present invention also provides polynucleotides encoding the polypeptides of the invention described below. Since such polynucleotides will be useful as sequences for recombinant production of polypeptides of the invention, it is not necessary for them to be capable of hybridising to the sequence of SEQ ID No. 1, although this will generally be desirable. Otherwise, such polynucleotides may be labelled, used, and made as described above if desired. DNA fragments may be prepared by using the PCR technique with specific primers.[33,34]

B. Polypeptides

The present invention relates to an (e.g. (substantially) purified and/or isolated) xylanase and variants thereof. The polypeptides of the invention may consist essentially of the amino acid sequence of SEQ ID No. 2, or a part of it (such as the mature sequence from positions 23 to 408), or a variant thereof. Polypeptides may also be encoded by a polynucleotide of the invention as described above. References to SEQ. ID. No. 2 can be substituted with the mature sequence only (residues $Ala^{23}$ to $Leu^{408}$) unless the context requires otherwise.

The polypeptides of the invention can be active on both arabinoxylan and aryl-β-D-xylosides (such as have arabinoxylanase and xylosidase activity).

A polypeptide of the invention may be in an isolated or a substantially purified form.

It will be understood that the polypeptide may be mixed with carriers or diluents which will not interfere with the intended purpose and/of function of the polypeptide and still be regarded as substantially isolated. It will generally comprise the polypeptide in a preparation in which more than 20%, e.g. more than 30%, 40%, 50%, 80%, 90%, 95% or 99%, by weight of the polypeptide in the preparation is a polypeptide of the invention. These are relatively pure compositions: for some applications the polypeptide may be present in the composition at up to 10%, 5%, 2%, 1% or even no more than 0.5%. Routine methods can be employed to purify and/or synthesise the proteins according to the invention[1]. For some formulations (e.g. for non-pharmaceutical uses) the amount of polypeptide present may be small, for example from 0.01 to 10%, such as from 0.1 to 5%, or 2% or even from 0.2 to 1%.

Preferably, the polypeptide of the invention is obtainable from a microorganism which possesses a gene encoding an enzyme with xylanase activity. More preferably the microorganism is a fungus, and optimally a filamentous fungi. Preferred organisms are thus of the genus *Talaromyces*, such as of the species *Talaromyces emersonfi* (e.g. CBS 393.64 or 814.70).

Activity

A polypeptide of the invention can have one or more of the following features, namely it:

(1) possesses β-D-xylanase activity;

(2) has an optimum pH range of from 2 to 6, such as from 3 to 5, optimally from 3.5 to 5.0;

(3) has optimum activity at a temperature of from 50° C. to 95° C., such as 70 to 90° C., optimally from 75 to 85° C.;

(4) has a molecular weight (deglycosylated) of from 30 to 50 kDa, preferably from 35 to 45 kDa, optimally from 40 to 44 kDa or (glycosylated) of from 50 to 75 kDa, preferably from 55 to 70 kDa, optimally from 60 to 66 kDa; and/or (5) has an isoelectric point of from 3.0 to 3.6.

The polypeptide can have the activity of EC. 3.2.1.8. Preferably the polypeptide is from Family 10 (formerly F-type).

"Xylanase activity" is defined as the ability to cleave cellulose or a β-D-xylan polymer (for example as found in plants e.g. oat or barley). The activity thus allows cleavage of β-D-xylan, such as between adjacent xylopyranosyl terminal and/or non-terminal units. Preferably the cleavage occurs at a [xylopyranosyl (1-4) xylopyranosyl] linkage. The polypeptide may preferentially cleave in between two adjacent (e.g. non-substituted) units. It can thus have endo activity (i.e. be an endoxylanase). The substrate polymer may or may not be substituted. It may also have exo activity (i.e. be an exoxylanase), such as cleavage of terminal xylopyranosyl units. Preferably the polypeptide will not have glucanase activity.

Polypeptides of the invention may also be active (or display activity) on arabinoxylan. Arabinoxylan is a sub-set of xylan, with L-arabino-furanosyl side chains linked to the C-2 or C-3, or both, of the xylos main chain residues. Arabinoxylan has the CAS Registry No. 98513-12-3. It can have the structure (1→4)-β-D-xylan with 3-linked α-L-arabinose branches. This type of xylan is normally found in oat spelt xylan.

This activity is the ability to hydrolyse untreated arabinoxylan. This means that the arabinoxylan has not boon treated or modified, for example it has not been treated with an arabinofuranosidase. This enzyme can remove arabinose side chains. The polypeptides of the invention are able to hydrolyse (cleave) arabinoxylan that has not been prior treated with arabinofuranosidase.

Arabinoxylan can be found in oats spelts, and in this specification the activity of the polypeptide (EXU, as well as PAHBAH activity) is determined on arabinoxylan from wheat flour (with an arabinose:xylose ratio of 41:59). An assay for arabinoxylan (as the substrate) is described later in the Examples.

The polypeptides of the invention may also have xylosidase activity, for example be able to hydrolyse substituted (e.g. aryl)-β-D-xylosides (also known as xylopyranosides). For example, they may be able to hydrolyse 4-methylumbelliferyl-β-D-xylopyranoside (CAS Registry No. 6734-33-4, obtainable from Sigma Chemical Co). This activity is the ability to liberate the fluorescent marker form the substrate. It may also hydrolyse (be active on) 5-bromo-4-chloro-3-indoxyl-β-D-xylopyranoside (CAS Registry No. 207606-55-1). The combination of activity on both arabinoxylan and an aryl-β-D-xyloside is unusual[36,37] and is a novel combination of activities for a polypeptide having xylanase activity.

Variants and Homologues

A polypeptide of the invention can comprise the amino acid sequence set out in SEQ ID No. 2 or a substantially homologous sequence, or a fragment of either sequence and can have xylanase activity. In general, the naturally occurring amino acid sequence shown in SEQ ID No. 2 is preferred.

In particular, the polypeptide of the invention may comprise:

a. the (mature) polypeptide sequence of SEQ ID No. 2 (residues 23 to 408) or the entire sequence of SEQ ID No. 2;

b. a naturally occurring variant or species homologue thereof; or c. a protein with at least 70, at least 75, at least 80, at least 90, at least 95, at least 98 or at least 99% sequence identity to (a) or (b).

A variant may be one that occurs naturally, for example in fungal, bacteria, yeast or plant cells and which can function in a substantially similar manner to the protein of SEQ ID No. 2, for example it has xylanase activity. Similarly a species homologue of the protein will be the equivalent protein which occurs naturally in another species and which can function as a xylanase. Variants include allelic variants either from the same strain as the polypeptide of the invention or from a different strain, but of the same genus, or of the same species.

Variants and species homologues can be obtained by following the procedures described herein for the production of the polypeptide of SEQ ID No. 2 and performing such procedures on a suitable cell source, for example a bacterial, yeast, fungal or plant cell. It will also be possible to use a probe as defined above to probe libraries made from yeast, bacterial, fungal or plant cells in order to obtain clones including the variants or species homology. The clones can be manipulated by conventional techniques to generate a polypeptide of the invention which can then be produced by recombinant or synthetic techniques known per se.

The polypeptide of the invention preferably has at least 70% sequence identity to the protein of SEQ ID No. 2, more preferably at least 80%, at least 90%, at least 95%, at least 97% or at least 99% sequence identity thereto, for example over a region of at least 40, 60, 100, 150, 200, 300 or 400 contiguous amino acids or over the full length of SEQ ID No. 2.

The sequence of the polypeptide of SEQ ID No. 2 and of variants and species homologues can thus be modified to provide polypeptides of the invention. Amino acid substitutions may be made, for example from or up to 1, 2 or 3 to 10, 20, 30, 50 or 100 substitutions. The same number of deletions or insertions may also be made. These changes may be made outside regions critical to the function of the polypeptide and so may still result in an active enzyme. The modified polypeptide generally retains activity as a xylanase.

Polypeptides of the invention include fragments of the above mentioned full length polypeptides and of variants thereof, including fragments of the sequence set out in SEQ ID No. 2. Such fragments typically retain activity as a xylanase. Fragments may be at least 50, 60, 70, 80, 100, 150, 200 or 250 amino acids long or may be this number of amino acids short of the fall length sequence (shown in SEQ ID No. 2). Fragments or variants comprise or represent a β-D-xylan binding region or a β-D-xylan cleaving region.

Polypeptides of the invention can if necessary be produced by synthetic means although usually they will be made recombinantly as described below. They may be modified for example by the addition of histidine residues or a T7 tag to assist their identification or purification or by the addition of a signal sequence to promote their secretion from a cell.

The term "variants" refers to polypeptides which can have the same essential character or basic biological functionality as the xylanase, and include allelic variants. The essential character of xylanase is that it is an enzyme that can cleave 1→4 links in β-D-xylan. A polypeptide having the same essential character as the xylanase may be identified by using a cellulose degradation assay as described later.

Variants of SEQ ID No. 2 also include sequences which vary from SEQ ID No. 2 but which are not necessarily derived from the naturally occurring xylanase protein. These variants may be described as having a % homology to SEQ ID No. 2 or having a number of substitutions within this sequence. Alternatively a variant may be encoded by a polynucleotide which hybridizes to SEQ ID No 1.

The variants can be defined in a similar manner to the variants of SEQ ID No. 1. Thus the variants may comprise variant sequences derived from other strains of *Talaromyces*. Other variants can be identified from other *Talaromyces* strains by looking for xylanase activity and cloning and sequencing as before. Variants may include the deletion, modification or addition of single amino acids or groups of amino acids within the protein sequence, as long as the peptide maintains the basic biological functionality of the xylanase.

Conservative substitutions may be made, for example according to the following Table. Amino acids in the same block in the second column and preferably in the same line in the third column may be substituted for each other. Preferably substitutions do not affect the folding or activity of the polypeptide.

| ALIPHATIC | Non-polar | G A P |
|           |           | I L V |
|           | Polar-uncharged | C S T M |
|           |           | N Q |
|           | Polar-charged | D E |
|           |           | K R |
| AROMATIC  |           | H F W Y |

Modifications

Polypeptides of the invention may be chemically modified, e.g. post translationally modified. For example, they may be glycosylated (one or more times, by the same or different sugars) or comprise modified amino acid residues. They may also be modified by the addition of histidine residues (to assist their purification) or by the addition of a signal sequence (to promote insertion into the cell membrane). The polypeptide may have one or more (N) amino- or (C) carboxyl-terminal extensions, such as an amino-terminal methionine residue, a small linker peptide of up to about 20-25 residues, or a (small) extension that facilitates purification, such as a poly-histidine or T7 tag, an antigenic epitope or a (e.g. maltose) binding domain[14] (e.g. at the C-terminus). These extensions may or may not be added via a linker.

A polypeptide of the invention may be labelled with a revealing label. The revealing label may be any suitable label which allows the polypeptide to be detected. Suitable labels include radioisotopes, e.g. $^{125}$I, $^{35}$S, enzymes, antibodies, polynucleotides and linkers such as biotin.

The polypeptides may be modified to include non-naturally occurring amino acids or to increase the stability of the polypeptide. When the proteins or peptides are produced by synthetic means, such amino acids may be introduced during production. The proteins or peptides may also be modified following either synthetic or recombinant production.

The polypeptides of the invention may also be produced using, or comprise (one or more) D-amino acids. In such cases the amino acid residues can be linked using the conventional N to C sequence as described in this application.

A number of side chain modifications are known in the art and may be made to the side chains of the proteins or peptides of the present invention. Such modifications include, for example modifications of amino acids by reductive alkylation by reaction with an aldehyde followed by reduction with $NaBH_4$, amidination with methylacetimidate or acylation with acetic anhydride.

The sequences provided by the present invention may also be used as starting materials for the construction of "second generation" enzymes. "Second generation" xylanases can be those that have been altered by mutagenesis techniques (e.g. site-directed mutagenesis), which have properties that differ from those of wild-type xylanases or recombinant xylanases such as those produced by the present invention. For example, the temperature or pH optimum, specific activity, substrate affinity or thermostability may be altered so as to be better suited for application in a defined process.

Amino acids essential to the activity of the xylanases of the invention, and therefore preferably subject to substitution, may be identified according to procedures known in the art, such as site-directed mutagenesis or alanine-scanning mutagenesis[10]. In the latter technique mutations are introduced at every residue in the molecule, and the resultant mutant molecules are tested for biological activity (e.g. xylanase activity) to identify amino acid residues that are critical to the activity of the molecule. Sites of enzyme-substrate interaction can also be determined by analysis of crystal structure as determined by such techniques as nuclear magnetic resonance, crystallography or photo-affinity labelling[11,12,13], or molecular modelling.

The use of yeast and fungal host cells is expected to provide for such post-translational modifications (e.g. proteolytic processing, myristilation, glycosylation, truncation, and tyrosine, serine or threonine phosphorylation) as may be needed to confer optimal biological activity on recombinant expression products of the invention.

Polypeptides of the invention may be provided in a form such that they are outside their natural cellular environment. Thus, they may be substantially isolated or purified, as discussed above, or in a cell in which they do not occur in nature, e.g. a cell of other fungal species, animals, yeast or bacteria.

C. Recombinant Aspects

The invention also provides vectors comprising a polynucleotide of the invention, including cloning and expression vectors, and methods of growing, transforming or transfecting such vectors in a suitable host cell, for example under conditions in which expression of a polypeptide of the invention occurs. Provided also are host cells comprising a polynucleotide or vector of the invention wherein the polynucleotide is heterologous to the genome of the host cell. The term "heterologous", usually with respect to the host cell, means that the polynucleotide does not naturally occur in the genome of the host cell or that the polypeptide is not naturally produced by that cell. Preferably, the host cell is a yeast cell, for example a yeast cell of the genus *Kluyveromyces* or *Saccharomyces* or a fungal cell, for example of the genus *Aspergillus*.

Polynucleotides of the invention can be incorporated into a recombinant replicable vector, for example a cloning or expression vector. The vector may be used to replicate the nucleic acid in a compatible host cell. Thus in a further embodiment the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

Vectors

The polynucleotide of the invention may inserted into an expression cassette. The vector into which the expression cassette or polynucleotide of the invention is inserted may be any vector which may conveniently be subjected to recombinant DNA procedures, and the choice of the vector will often depend on the host cell into which it is to be introduced. Thus, the vector may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

Preferably, a polynucleotide of the invention in a vector is operably linked to a regulatory sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence such as a promoter, enhancer or other expression regulation signal "operably linked" to a coding sequence is positioned in such a way that expression of the coding sequence is achieved under condition compatible with the control sequences or the sequences are arranged so that they function in concert for their intended purpose, for example transcription initiates at a promoter and proceeds through the DNA sequence encoding the polypeptide.

The vector may be a plasmid, cosmic, virus or phage vector, usually provided with an origin of replication, optionally a promoter for the expression of the polynucleotide and optionally an enhancer and/or a regulator of the promoter. A terminator sequence may be present, as may be a polyadenylation sequence. The vector may contain one or more selectable marker genes, for example an ampicillin resistance gene (in the case of a bacterial plasmid) or a neomycin resistance gene (for a mammalian vector). Vectors may be used in vitro, for example for the production of RNA or used to transfect or transform a host cell. They may comprise two or more polynucleotides of the invention, for example for overexpression.

The DNA sequence encoding the polypeptide is preferably introduced into a suitable host as part of an expression cassette (or construct) in which the DNA sequence is operably linked to expression signals which are capable of directing expression of the DNA sequence in the host cells. For transformation of the suitable host with the expression construct transformation procedures are available which are well known to the skilled person[3,4]. The expression construct can be used for transformation of the host as part of a vector carrying a selectable marker, or the expression construct may be co-transformed as a separate molecule together with the vector carrying a selectable marker. The vector may comprise one or more selectable marker genes.

Preferred selectable markers[15,16], include but are not limited to those that complement a defect in the host cell or confer resistance to a drug. They include e.g. versatile marker genes that can be used for transformation of most filamentous fungi and yeasts such as acetamidase genes or cDNAs (the amdS, niaD, facA genes or cDNAs from *A. nidulans, A. oryzae*, or *A. niger*), or genes providing resistance to antibiotics like G418, hygromycin, bleomycin, kanamycin, phleomycin or benomyl resistance (benA). Alternatively, specific selection markers can be used such as auxotrophic markers which require corresponding mutant host strains: e.g. URA3 (from *S. cerevisiae* or analogous genes from other yeasts), pyrG or pyfA (from *A. nidulans* or *A. niger*), argB (from *A. nidulans* or *A. niger*) or trpC. In a preferred embodiment the selection marker is deleted from the transformed host cell after introduction of the expression construct so as to obtain transformed host cells capable of producing the polypeptide which are free of selection marker genes[21,22].

Other markers include ATP synthetase, subunit 9 (oliC), orotidine-5'-phosphate-decarboxylase (pvrA), the bacterial (G418 resistance gene (this may also be used in yeast, but not in fungi), the ampicillin resistance gene (*E. coli*), the neomycin resistance gene (Bacillus) and the *E. coli* uidA gene, coding for β-glucuronidase (GUS). Vectors may be used in vitro, for example for the production of RNA or used to transfect or transform a host cell.

For most filamentous fungi and yeast, the vector or expression construct is preferably integrated in the genome of the host cell in order to obtain stable transformants. However, for certain yeasts also suitable episomal vectors are available into which the expression construct can be incorporated for stable and high level expression, examples thereof include vectors derived from the 2µ and pKD1 plasmids of *Saccharomyces* and *Kluyveromyces*, respectively, or vectors containing an AMA sequence (e.g. AMA1 from *Aspergillus*[3,20]). In case the expression constructs are integrated in the host cells genome, the constructs are either integrated at random loci in the genome, or at predetermined target loci using homologous recombination, in which case the target loci preferably comprise a highly expressed gene. A highly expressed gene is a gene whose mRNA can make up at least 0.01% (w/w) of the total cellular mRNA, e.g. under induced conditions, or alternatively, a gene whose gene product can make up at least 0.2% (w/w) of the total cellular protein, or, in case of a secreted gene product, can be secreted to a level of at least 0.05 g/l. A number of examples of suitable highly expressed genes are provided below.

A vector or expression construct for a given host cell may comprise the following elements operably linked to each other in a consecutive order from the 5'-end to 3'-end relative to the coding strand of the sequence encoding the polypeptide of the first invention:

(1) a promoter sequence capable of directing transcription of the DNA sequence encoding the polypeptide in the given host cell;

(2) optionally, a signal sequence capable of directing secretion of the polypeptide from the given host cell into a culture medium;

(3) a DNA sequence encoding a mature and preferably active form of the polypeptide; and preferably also (4) a transcription termination region (terminator) capable of terminating transcription downstream of the DNA sequence encoding the polypeptide.

Downstream of the DNA sequence encoding the polypeptide there may be a 3' untranslated region containing one or more transcription termination sites (e.g. a terminator). The origin of the terminator is less critical. The terminator can e.g. be native to the DNA sequence encoding the polypeptide. However, preferably a yeast terminator is used in yeast host cells and a filamentous fungal terminator is used in filamentous fungal host cells. More preferably, the terminator is endogenous to the host cell (in which the DNA sequence encoding the polypeptide is to be expressed).

Enhanced expression of the polynucleotide encoding the polypeptide of the invention may also be achieved by the selection of heterologous regulatory regions, e.g. promoter, secretion leader and/or terminator regions, which may serve to increase expression and, if desired, secretion levels of the protein of interest from the expression host and/or to provide for the inducible control of the expression of the polypeptide of the invention.

Aside from the promoter native to the gene encoding the polypeptide of the invention, other promoters may be used to direct expression of the polypeptide of the invention. The promoter may be selected for its efficiency in directing the expression of the polypeptide of the invention in the desired expression host.

Promoters/enhancers and other expression regulation signals may be selected to be compatible with the host cell for which the expression vector is designed. For example prokaryotic promoters may be used, in particular those suitable for use in *E. coli* strains. When expression is carried out in mammalian cells, mammalian promoters may be used. Tissues-specific promoters, for example hepatocyte cell-specific promoters, may also be used. Viral promoters may also be used, for example the Moloney murine leukaemia virus long terminal repeat (MMLV LTR), promoter rouse sarcoma virus (RSV) LTR promoter, SV40 (e.g. large T antigen) promoter, human cytomegalovirus (CMV) IE promoter, herpes simplex virus promoters or adenovirus promoters, HSV promoters such as the HSV IE promoters), or HPV promoters, particularly the HPV upstream regulatory region (URR). Yeast promoters include *S. cerevisiae* GAL4 and ADH promoters, the *S. pombe* nmt 1 and adh promoter. Mammalian promoters include the metallothionein promoter which may be induced in response to heavy metals such as cadmium and β-actin promoters. Tissue-specific promoters, in particular endothelial or neuronal cell specific promoters (for example the DDAHI and DDAHII promoters), are especially preferred.

A variety of promoters[15,16], can be used that are capable of directing transcription in the host cells of the invention. Preferably the promoter sequence is derived from a highly expressed gene as previously defined. Examples of preferred highly expressed genes from which promoters are preferably derived and/or which are comprised in preferred predetermined target loci for integration of expression constructs, include but are not limited to genes encoding glycolytic enzymes such as triose-phosphate isomerases (TPI), glyceraldehyde-phosphate dehydrogenases (GAPDH), phosphoglycerate kinases (PGK), pyruvate kinases (PYK or PKI), alcohol dehydrogenases (ADH), as well as genes encoding amylases, glucoamylases, proteases, xylanases, cellobiohydrolases, β-galactosidases, alcohol (methanol) oxidases elongation factors and ribosomal proteins. Specific examples of suitable highly expressed genes include e.g. the LAC4 gene from *Kluyveromyces* sp., the methanol oxidase genes (AOX and MOX) from *Hansenula* and *Pichia*, respectively, the glucoamylase (glaA) genes from *A. niger* and *A. awamori*, the *A. oryzae* TAKA-amylase gene, the *A. nidulans* gpdA gene and the *T. reesei* cellobiohydrolase genes.

Examples of strong constitutive and/or inducible promoters which are preferred for use in fungal expression hosts[15,16,35] are those which are obtainable from the fungal genes for xylanase (xlnA), phytase, ATP-synthetase, subunit 9 (oliC), triose phosphate isomerase (tpi), alcohol dehydrogenase (AdhA), α-amylase (amy), amyloglucosidase (AG—from the glaA gene), acetamidase (amdS) and glyceraldehyde-3-phosphate dehydrogenase (gpd) promoters.

Examples of strong yeast promoters are those obtainable from the genes for alcohol dehydrogenase, lactase, 3-phosphoglycerate kinase and triosephosphate isomerase.

Examples of strong bacterial promoters are the α amylase and SPo2 promoters as well as promoters from extracellular protease genes.

The native promoter of the gene encoding a xylanase may be replaced by a promoter that is regulated differently than the native promoter.

Promoters suitable for plant cells include napaline synthase (nos), octopine synthase (ocs), mannopine synthase (mas), ribulose small subunit (rubisco ssu), histone, rice actin, phaseolin, cauliflower mosaic virus (CMV) 35S and 19S and circovirus promoters. All these promoters are readily available in the art.

The vector may further include sequences flanking the polynucleotide giving rise to RNA which comprise sequences homologous to eukaryotic genomic sequences, preferably mammalian genomic sequences, or viral genomic sequences. This will allow the introduction of the polynucleotides of the invention into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors[18,19] and retroviruses, including lentiviruses, adenoviruses, adeno-associated viruses and HPV viruses (such as HPV-16 or HPV-18). Gene transfer techniques using these viruses are known to those skilled in the art. Retrovirus vectors for example may be used to stably integrate the polynucleotide giving rise to the antisense RNA into the host genome. Replication-defective adenovirus vectors by contrast remain episomal and therefore allow transient expression.

The vector may contain a polynucleotide of the invention oriented in an antisense direction to provide for the production of antisense RNA. This may be used to reduce, if desirable, the levels of expression of the polypeptide.

Host Cells and Expression

In a further aspect the invention provides a process for preparing a polypeptide according to the invention which comprises cultivating a host cell (e.g. transformed or transfected with an expression vector as described above) under conditions to provide for expression (by the vector) of a coding sequence encoding the polypeptide, and optionally recovering the expressed polypeptide. Polynucleotides of the invention can be incorporated into a recombinant replicable vector, e.g. an expression vector. The vector may be used to replicate the nucleic acid in a compatible host cell. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell. Suitable host cells include bacteria such as E. coli, yeast, mammalian cell lines and other eukaryotic cell lines, for example insect cells such as Sf9 cells and (e.g. filamentous) fungal cells.

Preferably the polypeptide is produced as a secreted protein in which case the DNA sequence encoding a mature form of the polypeptide in the expression construct is operably linked to a DNA sequence encoding a signal sequence. Preferably the signal sequence is native (homologous) to the DNA sequence encoding the polypeptide. Alternatively the signal sequence is foreign (heterologous) to the DNA sequence encoding the polypeptide, in which case the signal sequence is preferably endogenous to the host cell in which the DNA sequence is expressed. Examples of suitable signal sequences for yeast host cells are the signal sequences derived from yeast α-factor genes. Similarly, a suitable signal sequence for filamentous fungal host cells is e.g. a signal sequence derived from a filamentous fungal amyloglucosidase (AG) gene, e.g. the A. niger glaA gene. This may be used in combination with the amyloglucosidase (also called (gluco) amylase) promoter itself, as well as in combination with other promoters. Hybrid signal sequences may also be used with the context of the present invention.

Preferred heterologous secretion leader sequences are those originating from the fungal amyloglucosidase (AG) gene glaA—both 18 and 24 amino acid versions e.g. from Aspergillus), the α-factor gene (yeasts e.g. Saccharomyces and Kluyveromyces) or the a-amylase gene (Bacillus).

The vectors may be transformed or transfected into a suitable host cell as described above to provide for expression of a polypeptide of the invention. This process may comprise culturing a host cell transformed with an expression vector as described above under conditions to provide for expression by the vector of a coding sequence encoding the polypeptide.

A further aspect of the invention thus provides host cells transformed or transfected with or comprising a polynucleotide or vector of the invention. Preferably the polynucleotide is carried in a vector for the replication and expression of the polynucleotide. The cells will be chosen to be compatible with the said vector and may for example be prokaryotic (for example bacterial), fungal, yeast or plant cells.

A heterologous host may also be chosen wherein the polypeptide of the invention is produced in a form which is substantially free from other cellulose-degrading enzymes. This may be achieved by choosing a host which does not normally produce such enzymes such as Kluyveromyces lactis.

The invention encompasses processes for the production of the polypeptide of the invention by means of recombinant expression of a LANA sequence encoding the polypeptide. For this purpose the DNA sequence of the invention can be used for gene amplification and/or exchange of expression signals, such as promoters, secretion signal sequences, in order to allow economic production of the polypeptide in a suitable homologous or heterologous host cell. A homologous host cell is a host cell which is of the same species or which is a variant within the same species as the species from which the DNA sequence is derived.

Suitable host cells are preferably prokaryotic microorganisms such as bacteria, or more preferably eukaryotic organisms, for example fungi, such as yeasts or filamentous fungi, or plant cells. In general, yeast cells are preferred over fungal cells because they are easier to manipulate. However, some proteins are either poorly secreted from yeasts, or in some cases are not processed properly (e.g. hyperglycosylation in yeast). In these instances, a fungal host organism should be selected.

The host cell may over-express the polypeptide, and techniques for engineering over-expression are well known[3]. The host may thus have two or more copies of the encoding polynucleotide (and the vector may thus have two or more copies accordingly).

Bacteria from the genus *Bacillus* are very suitable as heterologous hosts because of their capability to secrete proteins into the culture medium. Other bacteria suitable as hosts are those from the genera *Streptomyces* and *Pseudomonas*. A preferred yeast host cell for the expression of the DNA sequence encoding the polypeptide is of the genera *Saccharomyces, Kluyveromyces, Hansenula, Pichia, Yarrowia*, and *Schizosaccharomyces*. More preferably a yeast host cell is selected from the group consisting of the species *Saccharomyces cerevisiae, Kluyveromyces lactis* (also known as *Kluyveromyces marxianus* var. *lactis*), *Hansenula polymorpha, Pichia pastoris, Yarrowia lipolytica*, and *Schizosaccharomyces pombe*.

Most preferred are, however, (e.g. filamentous) fungal host cells. Preferred filamentous fungal host cells are selected from the group consisting of the genera *Aspergillus, Trichodernza, Fusarium, Disporotrichum, Penicillium, Acremonium, Neurospora, Thermoascus, Myceliophtora, Sporotrichum, Thielavia*, and *Talaromyces*. More preferably a filamentous fungal host cell is of the species *Aspergillus oryzae, Aspergillus sojae, Aspergillus nidulans*, or a species from the *Aspergillus niger* Group[23]. These include but are not limited to *Aspergillus niger, Aspergillus awamori, Aspergillus tubingensis, Aspergillus aculeatus, Aspergillus foetidus, Aspergillus nidulans, Aspergillus japonicus, Aspergillus oryzae* and *Aspergillus ficuum*, and further consisting of the species *Trichoderma reesei, Fusarium graminearum, Penicillium chrysogenum, Acremonium alabamense, Neurospora crassa, Myceliophtora thernaophilurri, Sporotrichum cellulophilum, Disporotrichum dimorphosphorum* and *Thielavia terrestris*. Examples of preferred expression hosts within the scope of the present invention are fungi such as *Aspergillus* species[24,25] and *Trichoderma* species; bacteria such as *Bacillus* species[26,27], e.g. *Bacillus subtilis, Bacillus licheniformis, Bacillus amyloliquefaciens, Pseudomonas* species; and yeasts such as *Kluyveromyces* species[28], e.g. *Kluyveronmyces lactis*[29] and *Saccharomyces* species, e.g. *Saccharomyces cerevisiae*.

Host cells according to the invention include plant cells, and the invention therefore extends to transgenic organisms, such as plants and parts thereof, which contain one or more cells of the invention. The cells may heterologously express the polypeptide of the invention or may heterologously contain one or more of the polynucleotides of the invention. The transgenic (or genetically modified) plant may therefore have inserted (e.g. stably) into its genome a sequence encoding one or more of the polypeptides of the invention. The transformation of plant cells can be performed using known techniques, for example using a Ti or a Ri plasmid from *Agrobacterium tumefaciens*. The plasmid (or vector) may thus contain sequences necessary to infect a plant, and derivatives of the Ti and/or Ri plasmids may be employed.

Alternatively direct infection of a part of a plant, such as a leaf, root or stem can be effected. In this technique the plant to be infected can be wounded, for example by cutting the plant with a razor or puncturing the plant with a needle or rubbing the plant with an abrasive. The wound is then innoculated with the Agrobacterium. The plant or plant part can then be grown on a suitable culture medium and allowed to develop into a mature plant. Regeneration of transformed cells into genetically modified plants can be achieved by using known techniques, for example by selecting transformed shoots using an antibiotic and by sub-culturing the shoots on a medium containing the appropriate nutrients, plant hormones and the like.[17]

Culture of Host Cells and Recombinant Production

The invention also includes cells that have boon modified to express the xylanase or a variant thereof. Such cells include transient, or preferably stable higher eukaryotic cell lines, such as mammalian cells or insect cells, lower eukaryotic cells, such as yeast and (e.g. filamentous) fungal cells or prokaryotic cells such as bacterial cells.

It is also possible for the proteins of the invention to be transiently expressed in a cell line or on a membrane, such as for example in a baculovirus expression system. Such systems, which are adapted to express the proteins according to the invention, are also included within the scope of the present invention.

According to the present invention, the production of the polypeptide of the invention can be effected by the culturing of microbial expression hosts, which have been transformed with one or more polynucleotides of the present invention, in a conventional nutrient fermentation medium.

The recombinant host cells according to the invention may be cultured using procedures known in the art. For each combination of a promoter and a host cell, culture condition are available which are conducive to the expression the DNA sequence encoding the polypeptide. After reaching the desired cell density or titre of the polypeptide the culture is stopped and the polypeptide is recovered using known procedures.

The fermentation medium can comprise a known culture medium containing a carbon source (e.g. glucose, maltose, molasses, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). Optionally, an inducer (e.g. cellulose, pectin, maltose, maltodextrin or xylogalacturonan) may be included.

The selection of the appropriate medium may be based on the choice of expression host and/or based on the regulatory requirements of the expression construct. Such media are known to those skilled in the art. The medium may, if desired, contain additional components favouring the transformed expression hosts over other potentially contaminating micro-organisms.

The fermentation can be performed over a period of 0.5-30 days. It may be a batch, continuous or fed-batch process, suitably at a temperature in the range of between 0 and 45° C. and, for example, at a pH between 2 and 10. Preferred fermentation conditions are a temperature in the range of between 20 and 37° C. and/or a pH between 3 and 9. The appropriate conditions are usually selected based on the choice of the expression host and the protein to be expressed.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means.

D. Uses of the Xylanase and Methods of Processing Plant or Cellulose (E.g. Xylan)-Containing Materials The polypeptides of the invention which possess xylanase activity may be used to treat fungal or plant material including plant pulp and plant extracts. For example, they may be used to treat cereals, vegetables, fruits or extracts thereof. Conveniently the polypeptide of the invention is combined with suitable (solid or liquid) carriers or diluents including buffers to produce a composition/enzyme preparation. The polypeptide may be attached to or mixed with a carrier, e.g. immobilized on a solid carrier. Thus the present invention provides in a further aspect a composition comprising a polypeptide of the invention. This may be in a form suitable for packaging, transport and/or storage, preferably where the xylanase activity is retained. Compositions may be of paste, liquid, emulsion, powder, flake, granulate, pellet or other extrudate form.

The composition may further comprise additional ingredients such as one or more enzymes, for example pectinases, including endo-arabinanase and rhamnogalacturonase, cellulases, (other) xylanases, galacturonases, mannanases and/or xyloglucanases. The polypeptide is typically stably formulated either in liquid or dry form. Typically, the product is made as a composition which will optionally include, for example, a stabilising buffer and/or preservative. The compositions may also include other enzymes capable of digesting plant material or cellulose, for example other cellulases, e.g. (β-D-) glucanases. For certain applications, immobilization of the enzyme on a solid matrix or incorporation on or into solid carrier particles may be preferred. The composition may also include a variety of other plant material-degrading enzymes, for example cellulases and other pectinases.

The polypeptides and compositions of the invention may therefore be used in a method of processing plant material to degrade or modify the cellulose constituents (e.g. xylan) of the cell walls of the plant or fungal material. Thus in a further aspect, the present invention provides a method of degrading or modifying a plant cell which method comprises contacting the plant or fungal cell with a polypeptide or composition of the invention.

The invention also provides a method of processing a plant material which method comprises contacting the plant material with a polypeptide or composition of the invention to degrade or modify the cellulose in the (plant) material. Preferably the plant material is a plant pulp or plant extract, such as juices.

In particular, the degradation preferably comprises cleaving of xylan subunits of a cellulose component of the plant cell wall. The plant material is preferably a cereal, vegetable, fruit or vegetable or fruit pulp or extract. The present invention further provides a processed plant material obtainable by contacting a plant material with a polypeptide or composition of the invention.

The present invention also provides a method for reducing the viscosity of a plant extract which method comprises contacting the plant extract with a polypeptide or composition of the invention in an amount effective in degrading cellulose (or xylan) contained in the plant extract.

Plant and cellulose-containing materials include plant pulp, parts of plants and plant extracts. In the context of this invention an extract from a plant material is any substance which can be derived from plant material by extraction (mechanical and/or chemical), processing or by other separation techniques. The extract may be juice, nectar, base, or concentrates made thereof. The plant material may comprise or be derived from vegetables, e.g., carrots, celery, onions, legumes or leguminous plants (soy, soybean, peas) or fruit, e.g., pome or seed fruit (apples, pears, quince etc.), grapes, tomatoes, citrus (orange, lemon, lime, mandarin), melons, prunes, cherries, black currants, redcurrants, raspberries, strawberries, cranberries, pineapple and other tropical fruits, trees and parts thereof (e.g. pollen, from pine trees), or cereal (oats, barley, wheat, maize, rice). The material (to be hydrolysed) may also be agricultural residues, such as sugar beet pulp, corn cobs, wheat straw, (ground) nutshells, or recyclable materials, e.g. (waste) paper.

The polypeptides of the invention can thus be used to treat plant material including plant pulp and plant extracts. They may also be used to treat liquid or solid foodstuffs or edible foodstuff ingredients, or be used in the extraction of coffee, plant oils, starch or as a thickener in foods.

Typically, the polypeptides of the invention are used as a composition/enzyme preparation as described above. The composition will generally be added to plant pulp obtainable by, for example mechanical processing such as crushing or milling plant material. Incubation of the composition with the plant will typically be carried out for at time of from 10 minutes to 5 hours, such as 30 minutes to 2 hours, preferably for about 1 hour. The processing temperature is preferably 10-55° C., e.g. from 15 to 25° C., optimally about 20° C. and one can use 10-300 g, preferably 30-70 g, optimally about 50 g of enzyme per ton of material to be treated. All the enzyme(s) or their compositions used may be added sequentially or at the same time to the plant pulp. Depending on the composition of the enzyme preparation the plant material may first be macerated (e.g. to a purée) or liquefied. Using the polypeptides of the invention processing parameters such as the yield of the extraction, viscosity of the extract and/or quality of the extract can be improved.

Alternatively, or in addition to the above, a polypeptide of the invention may be added to the raw juice obtained from pressing or liquefying the plant pulp. Treatment of the raw juice will be carried out in a similar manner to the plant pulp in respect of dosage, temperature and holding time. Again, other enzymes such as those discussed previously may be included. Typical incubation conditions are as described in the previous paragraph. Once the raw juice has been incubated with the polypeptides of the invention, the juice is then centrifuged or (ultra) filtered to produce the final product.

After treatment with the polypeptide of the invention the (end) product can be heat treated, e.g. at 100° C. for a time of from 1 minute to 1 hour, under conditions to partially or fully inactivate the polypeptide(s) of the invention.

A composition containing a polypeptide of the invention may also be used during the preparation of fruit or vegetable purees.

The polypeptide of the invention may also be used in brewing, wine making, distilling or baking. It may therefore used in the preparation of alcoholic beverages such as wine and beer. For example it may improve the filterability or clarity (of beers, wort or wine). The protein may assist in the removal of dissolved organic substances from broth or culture media, for example where distillery waste from organic origin is bioconverted into microbial biomass. The xylanase can improve filterability and/or reduce viscosity in glucose syrups, such as from cereals produced by liquefaction (e.g. with α-amylase).

In baking the polypeptide may improve the dough structure, modify its stickiness or suppleness, improve the loaf volume and/or crumb structure or impart better textural characteristics such as break, shread or crumb quality. The polypeptide may be added at an amount of from 100 to 3,000, such as from 150 to 2,000, optimally from 200 to 1,600, EXU/kg flour.

The polypeptides find use in a number of industrial areas due to their xylanase activity. These can include not only alcohol production, but also in biomethanation, in bread making and in baking, in dental hygiene (for example dental or oral compositions), in the treatment or manufacture of leather, in the manufacture of paper, in pharmaceuticals, in tea, in the preparation or treatment of textiles, and in the treatment of waste. One aspect of the invention is therefore a food or foodstuff comprising the polypeptide, such as an alcoholic beverage, bread, dough or tea. The polypeptide may be formulated into a suitable compositions for any of these uses. The polypeptide may be present in an aqueous composition (e.g. hot water), preferably with one or more fungicides, in order to treat plant material (e.g. bulbs), especially to control parasitic insects, mites and nematodes. As the polypeptides of the invention can degrade xylan they may be added to foods or foodstuffs (for example by consumption by humans). The invention also includes pharmaceutical and veterinary compositions that comprise the polypeptide of the invention and the pharmaceutically or veterinarily acceptable carrier.

Polypeptides of the invention may also display anti-fungal activity. They may be able to degrade fungal cell walls, and thus can be employed for fungal cell wall lysis, in order to open the cells. This may release intracellular proteins. In such a way the polypeptides may be used to prepare yeast and/or fungal extracts.

E. Animal Feeds

The invention additionally relates to foodstuffs or an animal feed composition or additive comprising one or more polypeptides of the invention. The polypeptide may be present in the feed at a concentration different from its natural concentration. Preferred amounts are from 0.6 to 35, such as 1.5 to 15, preferably 3 to 15, mg per kg feed. Suitably the polypeptide of the invention is present in the feed at from 1,000 to 50,000 EXU/kg feed, such as from 2,500 to 25,000 EXU/kg, optimally from 5,000 to 20,000 EXU/kg.

The invention also relates to a process for the preparation of an animal feed composition, the process comprising adding to one or more edible feed substance(s) or ingredient(s) suitably containing xylan, a polypeptide of the invention. The polypeptides can be added to the animal feed composition separately from the feed substances or ingredients, individually or in combination with other feed additives. The polypeptide can be an integral part of one of the feed substances or ingredients.

The polypeptides of the invention may also be added to animal feeds rich in cellulose to improve the breakdown of the plant cell wall leading to improved utilisation of the plant nutrients by the animal. The polypeptides of the invention may be added to the feed or silage if pre-soaking or wet diets are preferred. Advantageously, the polypeptides of the invention may continue to degrade cellulose in the feed in vivo. Fungal based polypeptides of the invention in particular generally have lower pH optima and are capable of releasing important nutrients in such acidic environments as the stomach of an animal. The invention thus also contemplates (e.g. animal) feeds or foodstuffs comprising one or more polypeptides of the invention.

The polypeptides of the invention may also be used during the production of milk substitutes (or replacers) from soy bean. These milk substitutes can be consumed by both humans and animals. A typical problem during the preparation of these milk substitutes is the high viscosity of the soy bean slurry, resulting in the need for an undesirable dilution of the slurry to a concentration of dry solids of 10 to 15%. An enzyme preparation containing a polypeptide of the invention can be added to, or during the processing of, the slurry, enabling processing at a higher concentration (typically 40 to 50%) dry solids. The enzyme may also be used in the preparation of savoury product(s), e.g. from soy bean.

The composition may additionally comprise (particularly when being formulated for use in animal feed) one or more ionophores, oxidising agents, surfactants, rumen protected amino acids, enzyme enhancers or enzymes which may be produced naturally in the gastro-intestinal tract of the animals to be fed.

When added to feeds (including silage) for ruminants or monogastric animals (e.g. poultry or swine) the feeds may comprise cereals such as barley, wheat, maize, rye or oats or cereal by-products such as wheat bran or maize bran, or other plant materials such as soy beans and other legumes. The enzyme(s) may significantly improve the break-down of plant cell walls which leads to better utilisation of the plant nutrients by the animal. As a consequence, growth rate and/or feed conversion may be improved. The polypeptides of the invention may be added to the feed (directly or as an additive or ingredient) or a treated feed ingredient (e.g. cellulose/xylan) may be added instead.

The protein may reduce the viscosity of the feed (containing xylan): the protein may continue to hydrolyse xylan in vivo. The proteins of the invention are particularly applicable to animal feeds as they may still be active under highly acidic conditions, such as in the stomach of animals.

A particularly preferred method for the (exogenous) addition of the modified xylanase is to add the polypeptide of the invention as transgenic plant material and/or (e.g. transgenic) seed. The polypeptide may thus have been synthesized through heterologous gene expression, for example the gene encoding the desired enzyme may be cloned in to a plant expression vector, under control of the appropriate plant expression signals, e.g. a tissue specific promoter, such as a seed specific promoter. The expression vector containing the gene encoding the polypeptide can be subsequently transformed into plant cells, and transformed cells can be selected for regeneration into whole plants. The thus obtained transgenic plants can be grown and harvested, and those parts of the plants containing the heterologous (to the plant) polypeptide can be included in one of the compositions, either as such or after further processing. General methods for the (heterologous) expression of enzymes in (transgenic) plants, including methods for seed-specific expression of enzymes, are known[30]. The heterologous polypeptide may be contained in the seed of the transgenic plants or it may be contained in other plant parts such as roots, stems, leaves, wood, flowers, bark and/or fruit. The plant may be a monocot or a dicot. Suitable plants include cereals, such as oats, barley, wheat, maize and rice. Preferably the polynucleotide of the invention is stably incorporated into the plant genome.

The addition of the polypeptide in the form of transgenic plant material, e.g. in transgenic seed may require the processing of the plant material so as to make the enzyme available, or at least improve its availability. Such processing techniques may include various mechanical (e.g. milling and/or grinding) techniques or thermomechanical treatments such as extrusion or expansion.

The present invention thus also relates to a process for promoting growth and/or feed conversion in a monogastric or non-ruminant animal, the process comprising feeding the animal polypeptide of the invention. Suitable animals include farm, monogastric and/or non-ruminant animals such as pigs (or piglets), poultry (such as chickens, turkeys), calves or veal or aquatic (e.g. marine) animals (for example fish).

Assays for Cellulose Degrading Enzymes

Also within the present invention is the use of polypeptides according to the invention in screening methods to identify compounds that may act as agonists or antagonists which may modulate the xylanase. In general terms, such screening methods may involve contacting a polypeptide of the invention with a test compound and then measuring activity or incubating a polypeptide of the invention with a test substance and then detecting any modulation of xylanase activity. Agents which bind to the polypeptides of the present invention can also be identified by binding assays.

Modulator activity can be determined by contacting cells expressing a polypeptide of the invention with a substance under investigation and by monitoring the effect mediated by the polypeptides. The cells expressing the polypeptide may be in vitro and preferably, the assay is carried out in vitro using cells expressing recombinant polypeptide.

The assays and substrates described herein have allowed identification and confirmation of xylanase activity. These assays can be used to detect other cellulose degrading enzymes, for example those with xylanase activity. The substrate that can be used for this assay can comprise xylan.

Another aspect of the invention relates to an assay for identifying or detecting a polypeptide which is able to degrade cellulose. The activity may be a xylanase, or, may be pectin lyase, polygalacturonase, esterase, cellulase, xyloglucanase, galactonase, arabinanase or rhamnogalacturonase. The assay may comprise:

(a) providing, as a substrate for a candidate compound (usually a polypeptide), a suitable substrate (as described); and (b) contacting the substrate with the candidate compound, and detecting whether any products of xylanase activity are produced.

The above assays can be employed to identify modulators of the xylanase activity. Such compounds may reduce the softening of fruit, which may allow better flavour and colour development of fruit and may also allow for longer shelf and/or shipping life. Thus these assays may be used to identify inhibitors of the polypeptides of the invention that may be able to inhibit fruit softening.

Preferred features and characteristics of one aspect of the invention are applicable to another aspect mutatis mutandis.

The invention will now be described with reference to the following Examples which are intended to be illustrative only and not limiting.

EXAMPLES

General Procedures

Standard molecular cloning techniques such as DNA isolation, gel electrophoresis, enzymatic restriction modifications of nucleic acids, Southern analyses, E. coli transformation, colony lifts and filter hybridisations etc., were performed using standard techniques.[1,2] Synthetic oligo deoxynucleotides were obtained from ISOGEN Bioscience (Maarssen, The Netherlands). DNA sequence analyses were performed on an Applied Biosystems 373A DNA sequencer, according to the supplier's instructions.

DNA labelling and hybridizations were conducted according to the ECL™ direct nucleic acid labeling and detection systems (Amersham LIFE SCIENCE, Little Chalfont, England) or according to the standard radioactive labeling techniques.[1]

Example 1

RNA Isolation from *T. emersonii* and Synthesis of cDNA

*T. emersonii* strain CBS 393.64 was fermented under xylan-inducing conditions. At several time points mycelium and culture supernatants were harvested by filtration using Miracloth filtration wrap. The mycelium was washed extensively with demineralized water and squeezed between paper towels to remove excessive water. Mycelium from selected time points (based on the cellulase measurements in culture supernatants) was frozen immediately in liquid nitrogen and ground to a fine powder using a mortar and pestle. The resulting powder was transferred to a sterile 50 ml tube and weighed: for every 1-1.2 g of ground mycelium 10 ml TRIzol reagent (Gibco/BRL) was added (max. 25 ml per tube). The mycelial powder was immediately solubilised by vigorous mixing (vortexing, 1 min), followed by 5 minutes at room temperature incubation with occasional mixing. A 0.2 (original TRIzol) volume of chloroform (thus 2 ml for every 10 ml TRIzol used originally) was added, vortexed and left at room temperature for 10 minutes. Subsequently, the mixture was centrifuged at 4° C., 6000 g for 30 minutes. The top aqueous phase was transferred to a fresh tube and total RNA was precipitated by addition of a 0.5 (original TRIzol) volume of isopropyl alcohol (thus 5 ml of isopropyl alcohol for every 10 ml TRIzol used originally). After 10 minutes of precipitation at room temperature, the RNA was recovered by centrifugation for 30 minutes at 6000 g. On removal of supernatant the RNA pellet was rinsed with one volume of 70% ethanol. After removal of the ethanol, the RNA pellet was air dried. The dried RNA pellet was dissolved in 3 ml GTS (100 mM Tris-Cl, pH 7.5, 4 M guanidium thiocyanate, 0.5% sodium lauryl sarcosinate) buffer. 10 µl of RNA solution was used to determine quality and concentration of nucleic acids.

Northern analysis was performed[3] and the isolated (RNA further purified.[1,3] For isolation of mRNA a modified protocol (using gravity flow instead of centrifugation) of the PHARMACIA purification kit (Cat no. 27-9258-02) was used.[3] For cDNA synthesis the STRATAGENE cDNA Synthesis KIT was used according to the instructions of the manufacturer, except for a number of optimisations for using the pGBFIN vectors with major changes as have been previously described.[3]

The amount of cDNA synthesised was estimated by TCA precipitation and subsequently analysed via electrophoresis in alkaline agarose gels.[3]

Example 2

Preparation of a cDNA Library from *T. emersonii* mRNA

The cDNA pool obtained in Example 1 was blunted, ligated with adapters and restriction enzyme digested.[3]

Cloning of the cDNA in the expression vector pGBFIN-11[3] requires the presence of a EcoRI site on the 5- and of an XhoI site on the 3'-end of the cDNA. Therefore, the first strand priming oligonucleotide and the adapter sequences used (Pharmacia) were chosen to meet the prerequisites set for the expression vector.

The cDNAs obtained were separated via size fractionation through a SEPHAROSE CL-2B matrix, upon which size of the individual pools obtained were analysed via non-denaturing gel electrophoresis[3]. Two pools of cDNAs, obtained via cut offs at 0.5 kb and 1.0 kb respectively, were selected for construction of the a cDNA library in pGBFIN-11. For the pGBFIN-11, a pool of completely double-digested (EcoRI-XhoI) pGBFIN-11 vector (background ligation<1%) was prepared. The selected cDNA pools were ligated into the pGBFIN-11 vector and transformed into *E. coli* XL 10-Gold bacterial cells to generate two primary cDNA libraries. Transformation frequencies of the two pools were both >1.0×10$^6$.

From a fraction of both the *E. coli* cDNA libraries, colonies were selected randomly and plasmid DNA was isolated. Analysis of this plasmid DNA demonstrated that both cDNA libraries had insert percentages between 90 and 95%.

Furthermore, colony lifts were performed from a fraction of the library and the generated filters were subsequently hybridised with the *T. emersonii* gpdA gene, encoding the glyceraldehyde-3-phosphate dehydrogenase gene. Next, plasmid DNA was isolated and via restriction analysis it was demonstrated that all plasmid contained single inserts in the correct orientation. Sequencing of the 5' ends of the cDNAs within these *T. emersonii* gpdA containing plasmids demonstrated that >85% was full length.

Example 3

Transformation of the Expression Library to *A. niger*

DNA was isolated from the *E. coli* cDNA library as described earlier. Total plasmid DNA was digested for 4 hours at 37° C. with NotI to remove *E. coli* derived plasmid sequences. After purification, the DNA was dissolved in sterile demineralised water.

Multiple *A. niger* DS2978 transformations were performed[3] using $1.5 \times 10^7$ to $3.0 \times 10^7$ protoplasts and 10 g of plasmid DNA per transformation. Transformants were selected for the presence of the amdS selection marker by growth on acetamide as the sole N-source. Since both the amdS selection marker and the cDNA expression cassette are present on the integrating fragment growth on acetamide is indicative for the presence of a cDNA expression cassette.

After approximately 7-10 days incubation at 30° C., 10,000 transformants were purified: the *Aspergillus niger* transformants were transferred robotically (Flexys™ colony picker automater) from the transformation plates towards 96 wells MTP Master Plates (MPs) containing 150 µl per well of solidified selective medium (SM) (per 1000 ml: 0.52 g KCl, 1.52 g $K_2HPO_4$, 0.52 g $MgSO_4$, 20 g glucose, 1 g acetamide, 0.1M MES buffer, 15 g agar, 1 ml of trace element solution (containing, per litre: 2.2 g $ZnSO_4/7H_2O$, 1.1 g $H_3BO_3$, 0.5 g $FeSO_4/7H_2O$, 0.17 g $CoCl_2/6H_2O$, 0.16 g $CuSO_4/5H_2O$, 0.15 g $NaMoO_4/2H_2O$, 5.0 g EDTA, pH 6.5) pH 5.5. The transformants were grown on SM for 5 days at 34° C. The thus generated set of MPs was used to inoculate MTPs for growth and subsequent enzyme detection and backup plates (BPs) of the cDNA library which were stored at −80° C.

Example 4

Analysis of the *T. emersonii* Expression Library 5 days-old grown MPs were used as replication template and replica plated on fresh selective medium (SM) plates, containing 0.075% of AZCL-xylan (containing per litre: 0.52 g KCl, 1.52 g $K_2HPO_4$, 0.52 g $MgSO_4$, 20 g glucose, 1 g acetamide, 0.1M MES buffer, 15 g agar 1 ml of trace element solution (per 1 litre: 2.2 g $ZnSO_4/7H_2O$, 1.1 g $H_3BO_3$, 0.5 g $FeSO_4/7H_2O$, 0.17 g $CoCl_2/6H_2O$, 0.16 g $CuSO_4/5H_2O$, 0.15 g $NaMoO_4/2H_2O$, 5.0 g EDTA, pH 6.5) pH 5.5, 0.75 g AZCL-xylan (Megazyme, Australia).

Once inoculated the plates were incubated at 34° C. for 48 hours and then for 6 hours at 65° C. The plates were scored before and after the high temperature incubation. The positive colonies exhibiting xylanase activity showed a blue diffuse halo.

The positive xylanase clones from this first screen were re-inoculated on fresh SM medium and grown for 5 days at 34° C. The thus-obtained template plate was then replicated on selective medium and on selective medium containing 0.075% (w/v) of AZCL-xylan (Megazyme). The AZCL-xylan plate was treated as previously described.

The SM plates were incubated for 48 hours at 34° C. and subsequently were filled up with a top-agar-containing oat spelt xylan (5 g agarose, 0.5 g oat spelt xylan (Sigma ref: X0627)) prepared in 1 litre of 50 mM phosphate buffer (pH 7). Once the top agar solidified, the plates were placed at 65° C. for 4 hours. For the activity visualization, the plates were stained with a Congo red solution (10 g Congo red in 1 liter phosphate buffer pH 7.0) for 15 minutes. The staining solution was discarded and the plates were washed with 1M NaCl. This washing step was repeated twice. Positive clones appeared by forming a pale clearance halo on the (Congo) red background. Finally, 9 positive xylanase clones were identified.

Xylanase producing *Aspergillus* transformants, as identified in the xylanase plate assay, were grown in shake flask fermentation[3]. Medium samples were taken after 5 days of fermentation and analysed for xylanase activity as follows.

Supernatant (pre-diluted when necessary) was diluted 5 times in 0.25M sodium acetate buffer, pH 4.5.20 µl of diluted supernatant was transferred to microtitre dishes and 50 µl substrate (4% (w/v) Remazol Brilliant Blue RBB-Xylan (dissolved at 70° C. in demineralized water) was added and mixed thoroughly by pipetting up and down. The reaction mixture was incubated for 30 minutes at room temperature. The reaction was stopped by addition of 200 µl 96% ethanol and incubation for 10 minutes at room temperature. After the reaction had been terminated the microtiter plates were centrifuged for 10 minutes at 2500 rpm in a Beckman GPK centrifuge at room temperature. 100 µl of the supernatant was transferred to a new microtitre dish and absorbance of the blue colour was measured spectrophotometrically at 620 nm in an Anthosreader (Proton and Wilton). Specific activity was calculated from a calibration curve using a xylanase standard dissolved in 0.25M sodium acetate buffer pH 4.5.

Example 5

Genetic Analysis of Positive Transformants

Positive (re-confirmed) transformants identified in Example 4 were grown on liquid medium, the mycelium was harvested and total (chromosomal) DNA was isolated using the Puregene Isolation System (Biozym B. V.) for DNA isolation from filamentous fungi. DNA Isolation and purification were performed according to the suppliers' protocol, but slightly modified: protein precipitation steps 3 and 4 were repeated.

Chromosomal DNA was used as a template in a PCR reaction using primers 12207 (SEQ ID No. 4) and 11937 (SEQ ID No. 3) to amplify the insert(s) present in the expression cassette integrated into the chromosomal DNA.

Direct PCRs on transformants were performed according to an adapted version of a known protocol[4] except that the mycelium obtained was subsequently treated with Glucanex™ (Novo Nordisk) at 5 mg/ml concentrations instead of the NOVOzyme.

PCR reactions contained eLONGase™ B buffer (Life Technologies, Breda, The Netherlands), dNTPs (200 µM of each), 1 µl eLONGase™ Enzyme Mix, 1*5 template, and 10-30 pmol of each oligo, in a final volume of 50 µl. The optimal amount of oligos was determined experimentally for each purchased batch. On average, 10 to 30 µmol was used. Reactions were performed with the following cycle conditions: 1× (2 min) 94° C., 35× (1 min 94° C., 1 min 55° C., 6 min 72° C.), 1× (7 min 72° C.). Samples were loaded on agarose gels for analyses of PCR products.

The thus obtained PCR product was subcloned in the *E. coli* pcr2.1 cloning vector (Invitrogen, according to the supplier's instructions), resulting in plasmid pGBXEA-1. The *E. coli* strain harbouring plasmid pGBXEA-1 has been deposited at the Centraal Bureau voor Schimmelcultures, Baarn, the Netherlands under accession number CBS 102183.

The subcloned PCR product was sequenced. The resulting nucleotide sequence of the coding region is depicted in SEQ ID NO 1 and the deduced amino acid sequence of the protein in SEQ ID NO 2. This protein has been named XEA.

Example 6

Characterisation of *Talaroymyces emersonii* Xylanase

Definition of Endo Xylanase Unif (EXU) for this Specification

The unit of xylanase activity (EXU) is defined as the amount of enzyme (endoI endo-1,4-β-xylanase from *Asp. niger*[31]) that liberates 4.53 μmol reducing sugars (measured as xylose equivalents) per minute under assay conditions. The assay conditions comprise: 5 mg/ml arabinoxylan from wheat flour (Megazyme, Australia, 2/11 Ponderosa Parade, Warriewood NSW 2101) in 100 mM sodium citrate buffer (pH 3.5), temperature 40° C., at a reaction time of 60 minutes. Reactions were stopped by adding 1 M NaOH. Detection was done calorimetrically at 420 nm after incubating the samples with Fe-III-hexacyanide for 15 minutes in boiling water. The hexacyanoferrate reagent was made up by dissolving 1.17 g KFe (CN) and 19.5 g anhydrous sodium carbonate in 1 litre of water.

Viscometric Assay

In addition to the above absolute determination of xylanase activity, a relative method was used that followed the decrease in viscosity of a solution of wheat arabinoxylan (Megazyme, Australia, 2/11 Ponderosa Parade, Warriewood NSW 2101) upon addition of a certain amount of enzyme. Wheat arabinoxylan was dissolved in 0.425M sodium citrate buffer (pH 3.5) to a concentration of 8.3 mg/ml. The substrate was incubated at 55° C. for 10 minutes. Subsequently a small amount of enzyme (in the range 0.01-0.05 Units/ml) was added and the reaction allowed to proceed. After 60 minutes reaction time the viscosity of the sample was determined relative to a reference which was incubated with a *Aspergillus niger* endo-xylanase[31] standard of known EXU activity. Absolute activities in EXU for the standard were determined by reducing sugar method using Fe-111-hexacyanide as described above. Viscosity was determined manually using a Haake falling ball viscosity apparatus.

Reducing Sugars Activity Analysis

Enzyme activity according to the XPU definition was measured by detecting reducing sugars using 4-hydroxybenzoic acid hydrazide (PAHBAH). One XPU of activity is defined as the amount of enzyme required to release one μmol reducing sugars produced per minute from wheat arabinoxylan at pH 5.0 and 60° C. during 15 minutes, using a calibration curve of D (+) xylose. This is a known assay[32] with a modification is to the PAHBAH reagent as follows: 0.05M trisodium citrate, 0.1M Na2SO3, 0.02M CaCl2, 0.5M NaOH and 0.1M p-hydroxybenzoic acid hydrazide (PAHBAH). Final pH was 12. The reagent containing PAHBAH in alkaline solution, stored at room temperature, are used within one day. The absorbance was measured at 420 nm. A blank was prepared by adding 100 μl 0.1 M sodium acetate buffer instead of enzyme solution. Xylanase activity was assayed by mixing 100 μl of (diluted) enzyme solution with 400 μl 0.35% wheat arabinoxylan (Megazyme) in 0.1 M sodium acetate buffer (pH 5.0). The Eppendorf cups with the substrate were pre-incubated for 5 minutes at 60° C. The reaction is started by adding the enzyme solution. After 15 minutes adding 1.0 ml PAHBAH-reagent terminates the reaction. The Eppendorf cups were heated for 5 minutes at 100° C. and then cooled on ice. Samples were centrifuged at the appropriate speed in order to spin down any solid materials e.g. 1 minute at full speed in a Beckman Microfuge E. The absorbance was measured at 420 nm. A blank was prepared by adding 100 μl instead of enzyme solution. The measuring range is 0.01-0.1 XPU/ml.

Purification of the Xylanase 10.45 g ammonium sulphate was added to 43 ml cell free broth and brought on a Ethyl Sepharose™ column using Äkta explorer 100 (Pharmacia Biotech) Column: 15 ETH Source (code 17-0146-01, Pharmacia Biotech) (D=1.6 cm, 1=4.8 cm, V=9.6 ml). The column was equilibrated with 100 mM sodium acetate and 40% saturated ammonium sulphate pH 5.0. Elution was using a linear gradient leading to 100 mM sodium acetate (pH 5.0) in 20 column volumes. Fraction size: 5 ml. Flow rate: 10 ml/minute. Wavelengths monitored: 280, 254,214 nm. The fractions were tested for xylanase and analysed on HPLC-Size Exclusion Chromatography (SEC).

The most pure xylanase fractions were added to a Sephacryl S200 column according to the following conditions. Equipment Äkta explorer 100 (Pharmacia Biotech). Column: HiPrep 16/60 Sephacryl S200 HR (Pharmacia Biotech). Equilibration and elution were performed with 100 mM sodium acetate (pH 5.0). Flow rate: 1 ml/min. Fraction size: 4 ml. Wavelengths monitored: 280,254,214 nm. The purity of the elution fractions was analysed by HPLC-SEC, SDS-PAGE and native PAGE.

Protein Concentration

The protein concentration was determined by measuring the OD280. The (mature) xylanase from *T. emersonii* contains 11 Trp residues (positions 72, 108, 115, 121, 148, 300, 302, 308, 322, 377 and 385) and 23 Tyr residues (positions 36, 51, 109, 141, 146, 161, 167, 169, 174, 192, 193, 196, 200, 218, 281, 306, 316, 326, 332, 348, 395, 403 and 404). The calculated molar extinction coefficient was 89530 $M^{-1} \cdot cm^{-1}$ The molecular weight was 41,637 g/mol. The OD280 for 1 mg/ml XEA was 2.15.

Specific Activity of the Xylanase from *T. emersonii* (XEA)

The specific activity was determined using the reducing sugar PAHBAH method at 40° C. and 60° C. The specific activity for XEA was 150 XPU and 500 XPU at these two temperatures respectively. Protein concentration was determined by analysis of OD280.

| Temperature (° C.) | Specific Activity (XPU/mg) |
|---|---|
| 40 | 150 |
| 60 | 500 |

N-Terminal Sequence

The N-terminal amino acid sequence of the purified mature XEA was found to be: Ala-Gly-Leu-Asn-Thr-Ala (in the mature sequence this first Ala residue is Ala[23] in SEQ. ID. No. 2).

Iso-Electric Point (IEP)

Equipment: Phast system (Pharmacia Biotech), IEF 3-9 Phastgels (Pharmacia Biotech). Gels were ran and stained (Coomassie) according to standard Phast system protocols provided by the manufacturer. The IEP determined by iso electric focussing using PhastGel IEF3-9 was about 3.3.

Molecular Weight

SDS-PAGE electroforesis was performed using the Phast system (Pharmacia Biotech), Phastgels (Pharmacia Biotech), SDS-buffer strips/native buffer strips (Pharmacia Biotech).

Sample treatment: one volume of buffer (500 mM Tris-HCl pH 6.8, 10% SDS, 0.1% Bromo-phenol blue) was mixed with 4 volumes of sample and boiled for 3 minutes. Gels were run and stained (Coomassie or Silver) according to standard Phast system methods. The molecular weight upon SDS-PAGE using molecular weight markers (Pharmacia) was about 63 kD. The molecular weight calculated on basis of amino acid composition is 41,637 Daltons.

In addition the molecular weight was determined by gel permeation chromatography using gel filtration molecular weight standards (BIORAD, cat. no. 151-1901). The molecular weight determined by High Performance SEC was 42 kD. (HP SEC was conducted using a TSK G3000SW (cat. no. 05103, Toso Haas) column. Samples were eluted in 0.1M sodium phosphate (pH7) at 1 ml/min at room temperature. Detection was performed at 280 nm). The high molecular weight as observed on SDS-PAGE, seems to be an overestimation. It is likely caused by glycosylation of the xylanase.

Deglycosylation

5 µl purified enzyme (ca. 5 mg/ml) was mixed with 20 µl 0.5% SDS and 25 µl 1% mercapto-ethanol. The mixture was boiled for 4 minutes. After cooling down, 20 µl N-glycosidase F (500 U/ml) and 20 µl 3% Triton X-100 in 1M sodium phosphate buffer (pH 7.0) was added. It was then incubated overnight at 37° C. and the deglycosylation analysed with SDS-PAGE. The amino acid sequence suggests 2 glycosylation sites (Asn[55] and Asn[123], see SEQ ID No. 2).

SDS-PAGE shows that the N-glycosidase F treated xylanase migrates further and the molecular weight is lower than the untreated or the pretreated (boiled with SDS and β-mercapto-ethanol) xylanase. So the surprisingly high molecular weight observed on SDS-PAGE is probably caused by glycosylation.

pH- and Temperature-Profile

The cell free broth was analysed for xylanase activity at different pH and temperatures. The xylanase activity was analysed with the reducing sugars method using PAHBAH at pH 4 at various temperatures (see Table 1A) or at 60° C. at different pH's (Table 1B). Table 1A shows that the temperature optimum of XEA is around 80° C. Table 1B shows that the pH optimum of XEA is between pH4 and pH 5 (there are two columns of figures as the experiments were conducted twice).

TABLE 1A

Xylanase Temperature Dependence

| Temperature (° C.) | Activity (µM xylose/15 min) | Relative Activity (%) |
|---|---|---|
| 30 | 20-30 | 10 |
| 40 | 40-50 | 19 |
| 50 | 90-100 | 40 |
| 60 | 120-130 | 52 |
| 70 | 195-205 | 83 |
| 80 | 235-245 | 100 |
| 90 | 65-75 | 29 |

TABLE 1B pH Dependence

| pH | Activity (µM xylose/15 minutes) | Activity (µM xylose/15 minutes) |
|---|---|---|
| 3.0 | 118.1 | 123.4 |
| 3.5 | 141.8 | 127.8 |
| 4.0 | 145.2 | 148.3 |
| 4.5 | 140.8 | 149.1 |
| 5.0 | 117.9 | 124.8 |
| 5.5 | 91.7 | 99.1 |
| 6.0 | 57.3 | 60.1 |

Thermostability

Differential Scanning Calorimetic (DSC) Analysis of Unfolding Temperature

The unfolding temperature of XEA was determined using DSC. The measuring conditions used were with sodium acetate buffer (pH 5), 2-4 mg/ml, and a heating rate of 2.5° C./min. The unfolding temperature (Td) of XEA was found to be 80.1° C.

T50 Measurement

T50 is the temperature at which 50% residual activity is left after 20 minutes of incubation and so is a measure for thermostability. The T50 incubations were performed as follows. The xylanase sample was diluted so that final xylanase concentration was within the measuring range for the PAHBAH test (XPU units). Then it was diluted with 0.1 M sodium acetate buffer (pH 5.0) containing 1 mg/ml BSA to avoid a-specific binding and denaturation at surfaces of the tubes. The buffer was pre-heated at 60, 70, 80, 85 and 90° C. in a thermomixers for 5 minutes and subsequently the xylanase added. The samples were heated for 20 minutes and cooled in ice. The activity was measured using the PAHBAH test.

In Table 2 the percentage of residual activity with respect to the non-incubated control after 20 minutes incubation at the given temperature is shown. From this table the T50 can be derived: it was 82° C.

TABLE 2

Thermostability of the XEA xylanase

| Temperature (° C.) | Residual Activity (1%) |
|---|---|
| 40 | 100 |
| 50 | 104 |
| 60 | 103 |
| 70 | 99 |
| 75 | 90 |
| 80 | 85 |
| 85 | 8 |
| 90 | 1 |

In addition T50 values were measured at different pHs and in the presence of EDTA. The results are presented in Table 3.

TABLE 3

Determination of influence pH and metal ions on the stability of XEA.

| pH | T50 (° C.) |
|---|---|
| 3 | 73 |
| 3.5 | 77 |
| 4 | 80 |
| 4.5 | 80 |
| 5 | 81 |

TABLE 3-continued

Determination of influence pH and metal ions on the stability of XEA.

| pH | T50 (° C.) |
|---|---|
| 5 (+EDTA) | 81 |
| 6 | 75 |
| 7[1] | <72 |
| 8[1] | <72 |

([1]pH 7 and 8: too few data points in the low temperature area)

XEA is most stable in the pH area pH 4 up to pH 5. Below pH 3.5 and above pH 5.5 the thermostability starts to decline but is still significantly better than most of the presently known fungal xylanases. The presence of EDTA does not influence the T50. This means that for stability XEA is not dependent on positive metal ions which are complexed by EDTA.

Example 7

Use of the *Talaromyces xylanase* (XEA) in Animal Feed

A trial was performed using male broilers (Cobb). From days 1 to 5 of age they were kept in floor pens and offered a commercial broiler-starter feed. At the age of 5 days, the animals were randomly distributed over 54 cages, based on their individual weights. 15 broilers were housed per cage from days 5-19 of age. At day 19, the number of animals per cage was reduced to 12. Six cages were allocated to one treatment. Since the cage is the experimental unit, this means that there were six replications per treatment.

The cages were set up in a artificially heated, illuminated and ventilated broiler house, using a three-tier cage system. Each cage had a floor space of 0.98 m², and had a wire floor. The room was illuminated 24 hours/day, but the light intensity was gradually decreased during the trial. Also the temperature was decreased gradually: from 28° C. during the first week to 23° C. during the last week. The humidity during the trial was kept at approximately 60%. Animals were vaccinated according to the normal vaccination program against Infectious Bronchitis and New Castle Disease.

Nine treatments were included in this trial. To a diet based on wheat (see Table 4) no enzyme was added (control), or a quantity equal to approximately 2500, 5000, 10000 or 25000 EXU/kg feed of either the *Talaromyces* endoxylanase (XEA) or an *Aspergillus niger* endoxylanase (EndoI, an endo-1,4-β-endoxylanase[31] commercially available from DSM N. V., Agri Ingredients, Delft, The Netherlands) as a control. The enzymes were added to the feed in the form of a granulated product that was mixed into a premix prior to mixing it into the diet. The diets were offered ad libitum to the animals in the form of a pellets. During the pelleting process the temperature of the pellets did not exceed approximately 70° C. Water was also available freely.

Body weight gain (BWG) and feed conversion ratio (FCR) were determined for the periods 5-19 days of age and 5-33 days of age.

TABLE 4

Feed composition and contents of main nutrients

| Ingredient | Content (%) |
|---|---|
| Wheat | 50.0 |
| Rye | 10.0 |
| Soybean meal | 20.0 |
| Full fat soybeans (toasted) | 1.5 |
| Manioc | 1.69 |
| Meat and bone meal | 5.5 |
| Fish meal | 2.0 |
| Blended animal fat | 6.0 |
| Mineral and vitamin premix* | 1.0 |
| Limestone | 0.85 |
| Monocalcium phosphate | 0.75 |
| Salt | 0.3 |
| L-lysine HCl | 0.16 |
| DL-methionine | 0.22 |
| L-threonine | 0.03 |
| $ME_{broilers}$ (MJ/kg) | 12.0 |
| Crude protein (%) | 21.4 |
| Crude fat (%) | 8.5 |
| Digestible lysine (%) | 1.06 |
| Digestible methionine + cysteine (%) | 0.78 |

*The diet contained vitamin and trace-mineral levels as common in the Netherlands. No antibiotic growth promoters nor coccidiostats were added to the diets.

The results of this trial are presented in Table 5 which shows the average BWG and FCR of the broilers in two periods. The enzyme additions are indicated in activity units (EXU). As the BWG increases, so the FCR decreases as FCR is the amount of feed (g) needed for growth.

TABLE 5

| | BWG (g/bird) | | FCR (g/g) | |
|---|---|---|---|---|
| | 5-19 days | 5-33 days | 5-19 days | 5-33 days |
| Control | 647 | 1665 | 1.486 | 1.749 |
| *Talaromyces* (XEA, invention) | | | | |
| +2500 EXU/kg | 668 | 1696 | 1,447 | 1.666 |
| +5000 EXU/kg | 683 | 1757 | 1.419 | 1.647 |
| +10000 EXU/kg | 662 | 1736 | 1.444 | 1.673 |
| +25000 EXU/kg | 676 | 1731 | 1.429 | 1.656 |
| *Aspergillus* Nigel Endol (for comparison) | | | | |
| +25000 EXU/kg | 682 | 1742 | 1.440 | 1.659 |
| +5000 EXU/kg | 682 | 1730 | 1.458 | 1.704 |
| +10000 EXU/kg | 672 | 1686 | 1.417 | 1.662 |
| +25000 EXU/kg | 696 | 1742 | 1.466 | 1.685 |

Both growth and FCR significantly ($P<0.05$) improved for the diets containing the enzymes, both after 14 days of experimental period as after the total experimental period. A few differences were observed between the different doses, but the XEA enzyme was as good as (if not better than) the commercially available enzyme.

Example 8

Baking Performance of the *Talaromyces emersonii* Endoxylanase (XEA)

Preparation of tin bread in a standard baking process was performed by mixing 3500 g wheat flour (a mix of 80% Kolibri and 20% Ibis wheat flours (Meneba, Holland) at about 21° C.), 77 g compressed (Konings) yeast, 70 g salt, 25 ppm ascorbic acid, 10 ppm fungal α-amylase Fermizyme™ $P_{200}$, (DSM N.V., Bakery Ingredients, Delft, The Netherlands) and different quantities of the endoxylanase XEA enzyme and 2030 mL water (8-15° C.) in a spiral mixer (Hobart) for 2 minutes (at speed 1) and for about 6 minutes (at speed 2) to put in 125 Wh (Watt-hours) of energy. The dough temperature was 28° C. Machineability of the dough was analysed by hand by a qualified baker.

Directly after mixing the dough was divided into 6 pieces each of 875 g, rounded and proofed for 35 minutes in a proofing cabinet at 34° C. and 85% RH (relative humidity). At the end of this period the doughs were shaped and panned and given a final proof of 75 minutes in a proofing cabinet at 38° C. and 87% RH. Afterwards the fully proofed doughs are baked in an electric oven at 210° C. for 30 minutes. After cooling to room temperature the volumes of the loaves of bread were determined by the rape seed displacement method. After 16-24 hours storage in sealed polyethylene bags at room temperature the crumb quality was assessed by a qualified baker. The results are shown in Table 6.

terms of loaf volume and in terms of crumb quality. Despite the large volumes of the loaves the crumb structure was still very regular and fine.

Example 9 and Comparative Example 10

Comparison of Baking Performance of the *Talaromyces emersonii* Enzyme (XEA) with Endoxylanase from *Asp niger*

The baking performance of XEA was compared in Dutch tin bread production with a currently used fungal endoxylanase from *Aspergillus niger*. This *A. niger* endoxylanase was supplied in its pure commercially available form, i.e. Fermizyme™ HSP$_{6000}$ Fermizyme™ HSP is a good enzyme for application in bread making, but it can introduce dough stickiness and does not always provide a sufficient loaf volume increase.

The exact procedure of Example 7 was repeated except different quantities of either the endoxylanase XEA or Fermizyme HSP$_{6000}$ were used.

The results are shown in Table 7.

TABLE 7

| Example No. | Dosage level (EXU/kg flour) | Loaf volume (mL) | (%) | Dough handling | Break & Shred (scale 0-10) | Crumb quality (scale 0-10) |
|---|---|---|---|---|---|---|
| 9: endoxylanase XEA | 0 | 4170 | 100 | Good, not sticky | 6 | 6 |
| | 264 | 4430 | 106 | Good, not sticky | 6.5 | 7.5 |
| | 528 | 4647 | 111 | Good, not sticky | 7 | 7.5 |
| | 1056 | 4761 | 114 | Supple, not sticky | 7.5 | 8 |
| | 1584 | 4880 | 117 | Supple, bit slack, Not sticky | 5# | 7.5 |
| 10: Fermizyme™ HSP$_{6000}$ | 0 | 4170 | 100 | Good, not sticky | 6 | 6 |
| | 264 | 4304 | 103 | Supple, not sticky | 6.5 | 6 |
| | 528 | 4355 | 104 | Supple, bit sticky | 6.5 | 7 |
| | 1056 | 4539 | 109 | Supple, sticky, bit slack | 7 | 7.5 |
| | 1584 | 4698 | 113 | Supple, sticky, bit slack | 7.5 | 8 | loaf volume was too large, so mushroom shape of bread was formed.

TABLE 6

| Dosage level of XEA (EXU/kg flour) | Loaf volume (mL) | (%) | Dough handling | Baking performance (scale 0-10) | Crumb quality (scale 0-10) |
|---|---|---|---|---|---|
| 0 | 4123 | 100 | Easy, not sticky | 6 | 6 |
| 176 | 4420 | 107 | Easier, not sticky | 7 | 7 |
| 527 | 4756 | 115 | Easier, not sticky | 7.5 | 7 |
| 1581 | 4794 | 116 | Easy, little bit sticky | 7.5 | 7.5 |

The quality of the doughs was very good. Only at the highest dose of endoxylanase XEA was a little stickiness experienced during handling of the dough. However this little stickiness did not influence the dough's machineability. All doughs containing endoxylanase XEA were very supple and easy to handle.

From these baking results it was concluded that endoxylanase XEA is very effective in improving bread quality, both in From the results it is clear that the endoxylanase XEA did not introduce stickiness in the dough, and improved loaf volume to a larger extent than obtained by introducing Fermizyme™ HSP. Moreover, less endoxylanase units/kg flour were needed to reach a certain level in loaf volume when XEA was used instead of Fermizyme™ HSP. Break and shred quality was similar at equivalent volumes. The crumb structure obtained by adding XEA was at least as good as obtained with Fermizymem™ HSP.

Overall, the endoxylanase XEA solves some of the problems in dough and bread making using Fermizyme™ HSP. No stickiness was introduced in the dough, the loaf volumes obtained were larger and the crumb structure, despite the larger volumes, was still very regular and fine.

Example 11

Pelletting Stability Trials

Corn starch (4543 g) was placed into an Erweka™ Z-kneader. Then 1069 g of an ultrafiltrate form fermentation containing the xylanase of the invention (batch XEA 502-8m, which had 43,553 EXU/g and 6.7% dry matter) was added to the starch during mixing to obtain a wet mixture that had around 15,000 EXU/g (when dried to 94% dry matter). After the liquid had been added, mixing was continued for a further 10 minutes.

In a vacuum drying chamber (40° C.) the mixture was dried for 12 hours to 94.5% dry matter. It was then milled in an Erweka™ Freewitt mill through a 1 mm screen. This was Example 11A.

The same recipe was repeated using Lyxasan™ Batch OP 0036 (containing the endo-1,4-β-endoxylanase[31] commercially available from DSM N. V., Agri Ingredients, Delft, The Netherlands). To 5885 g starch 1984 g of UF (ultrafiltrate) with 42,550 EXU/g and 3.7% dry matter was added. This mixture was dried to 94% dry matter and milled as in Example 11A (this forms Comparative Example 11B).

The third sample is a commercially coated product called Biofeed Wheat CT which is commercially available from Novo Nordisk, Denmark. This contains a G-type xylanase from *Thermomyces lanugihosis* and has a fat coating (Comparative Example 11C).

All three samples were tested in a pelletting trial at three different temperatures. To an animal feed (the composition is shown in Table 8 below), the enzyme mixture was added at two different concentrations, 0.24% (11A) and 0.1% (11B, 11C). After mixing the feed was steam heated in a conditioner up to 65° C., 75° C. or 85° C. and subsequently pelletted through a 65 mm thick die-plate with holes 5 mm in diameter. It was cooled down immediately. The residual activity in the pellets was then measured and the results of the stability tests are shown in Table 9.

TABLE 8

Composition of Animal Feed

| Raw Materials | Content (%) |
| --- | --- |
| Maize | 20.00 |
| Wheat | 30.00 |
| Soy Bean (heat treated) | 10.00 |
| Soy Bean (meal) (46.7 cp) | 22.50 |
| *Tapioca* | 5.07 |
| Fish Meal (70% cp) | 1.50 |
| Feather Meal (hydrolysed) | 1.00 |
| Soy Bean Oil | 1.30 |
| Animal Fat | 4.5 |
| Viitamin/Mineral Pre-mix (Maize) | 1.00 |
| Limestone | 1.300 |
| Monocalcium phosphate | 1.20 |
| Salt | 0.32 |
| L-lysine | 0.12 |
| DL-methionine | 0.19 |

TABLE 9

Pelletting Stabilities of the Enzymes

| Residual Activity (%) | Example 11A | Comparative Example 11B | Comparative Example 11C |
| --- | --- | --- | --- |
| 65° C. | 84 | 64 | 86 |
| 75° C. | 82 | 16 | 83 |
| 85° C. | 66 | 4 | 56 |

As can be seen, the stability at high temperature (85° C.) the XEA protein of the invention gave considerably better stability results than the currently marketed commercial product.

Example 12

Activity on Aryl-β-D-xylosides

The two substrates 5-bromo-4-chloro-3-indoxyl-β-D-xylopyranoside (CAS Reg No. 207606-55-1, also called X-b-D-xyl) and 4-umbelliferyl-β-D-xylopyrarloside (CAS Reg No. 6734-33-4, also called 4-MU-b-D-xyl) were utilized in order to screen for xylosidase activity. They were directly added to the medium. The strains composing the library were organized on the 96 wells plate format. That way, the master plate was replicated easily on detection media. The library was grown on selective medium (0.52 g/l KCl, 1.52 g/l K2HP04, 0.52 g/l MgSO4, 2% glucose, 10 mM acetamide, 1/1000 trace elements (2.2 g ZnS04/7H20, 1.1 g H3BO3, 0.5gFeSO4/7H20, 0.17 g CoCl2/6H20, 0.16 g CuS04/5H20, 0.15 g NaMo04/2H20, 5.0 g EDTA, pH adjusted at 6.5 with KOH and filter sterilized 0.45 µm), pH adjusted with KOH (ION to 6) containing either X-b-D-xyl or 4-MU-b-D-xyl (at a concentration of 200 mg/l and 150 mg/l respectively). X-b-D-xyl had previously been dissolved in a minimal volume of dimethyl formamide (DMF). The plates were incubated at 33° C. for 48 hours and then incubated for 6 hours at 65° C. The plates were scored before and after the 6 hr, 65° C. incubation. The X-xyl plates were analysed directly based on the presence (or not) of a turquoise blue halo which was found to be present. Detection of xylosidase activity on 4-MU-xyl plates was checked by placing the plate under 310 nm-wavelength UV light. Positive clones appeared surrounded by a blue fluorescent halo.

REFERENCES

1. Sambrook et al. (1989) "Molecular Cloning: A laboratory manual", 2nd Edition, Cold Spring Harbor Laboratories, Cold Spring Harbor, New York
2. Innis et al. (1990) "PCR protocols, a guide to methods and applications" Academic Press, San Diego.
3. WO-A-99/32617
4. van Zeijl, C. et al. (1998) J. of Biotechnol. 59: 221-224
5. Devereux et al (1984) *Nucleic Acids Research* 12, p387-395
6. Altschul S. F. (1993) J Mol Evol 36: 290-300
7. Altschul, S, F et al (1990) J Mol Biol 215: 403-10
8. Henikoff and Henikoff (1992) *Proc. Natl. Acad Sci. USA* 89: 10915-10919)
9, Karlin and Altschul (1993) Proc. Natl. Acad. Sci. USA 90: 5873-5787
10. Cunningham and Wells, Science, 244, 1081-1085, 1989
11. de Vos et al. (Science, 255,306-312, 1992)
12. Smith et al. (J. Mol. Biol., 224,899-904, 1992)
13. Wlodaver et al. (FEBS Lett., 309, 59-64, 1992)
14. Ford et al. Protein Expression and Purification, 2, 95-107, 1991
15. Goosen et al, "Transformation and Gene Manipulation in Filamentous Fungi: an overview" in: Handbook of Applied Mycology, Vol. 4 (1992)
16. Romanos et al, Yeast 8: 423-488 (1992)
17. EP-A-0,449,375
18. WO-A-98/04726
19. WO-A-98/30707

20. Alenkso and Clutterbuck, Fungal Genet. Biol 21: 373-397 (1997)
21. EP-A-0,635,574
22. WO-A-98/46772
23. Raper and Fennell, The Genus *Aspergillus*, The Williams & Wilkins Company, Baltimore, pp 293-344, 1965
24. EP-A-0,184,433
25. EP-A-0,284,603
26. EP-A-0,134,048
27. EP-A-0,253,455
28. EP-A-0,096,340
29. EP-A-0,301,670
30. EP-A-0,449,375
31. EP-A-0,463,706 (Gist-brocades B. V.)
32. Lever, M., Powell, J. C., Killip, M., Small, C. W. (1973) J. Lab. Clin. Med. 82: 649-655
33. U.S. Pat. No. 4,683,202
34. Saiki et al, Science 239: 487-491 (1988)
35. Davies et al, "*Aspergillus:* 50 years on", Progress in Industrial Microbiology, 29: 527-560 (1994)
36. Tuohy et al, Biochem J. 290: 515-523 (1993)
37. Tuohy et al, Bioresource Technology 50: 37-42 (1995)

(All documents described herein are incorporated by reference)

(All Documents Described Herein are Incorporated by Reference)

We claim:

1. An isolated polynucleotide comprising (a) a nucleic acid sequence comprising the sequence of SEQ ID NO: 1 or the complement thereof; (b) a nucleic acid sequence comprising the coding sequence from nucleotides 69 to 1224 of SEQ ID NO: 1 or the complement thereof; (c) a nucleic acid sequence encoding a polypeptide having xylanase activity comprising the amino acid sequence from amino acids 23 to 408 of SEQ ID NO: 2; (d) a nucleic acid sequence encoding a polypeptide having xylanase activity comprising an amino acid sequence having at least 95% sequence identity with the amino acid sequence from amino acids 23 to 408 of SEQ ID NO: 2; or (e) a nucleic acid sequence comprising a sequence having at least 95% identity to the coding sequence of SEQ ID NO: 1, wherein said nucleic acid encodes a polypeptide having xylanase activity.

2. The polynucleotide of claim 1, wherein the nucleic acid sequence comprises a sequence having at least 98% sequence identity to the coding sequence of SEQ ID NO: 1 which encodes a polypeptide having xylanase activity.

3. A vector comprising the polynucleotide of claim 1.

4. A vector comprising the polynucleotide of claim 1 operably linked to a regulatory sequence.

5. A host cell comprising the vector of claim 3, wherein the host cell is selected from a prokaryotic cell, a fungal cell, a yeast cell, a plant cell, or a eukaryotic cell line.

6. A process of producing a polypeptide comprising culturing the host cell of claim 5 under conditions that provide for expression of the polypeptide.

7. A host cell comprising the vector of claim 4, wherein the host cell is selected from a prokaryotic cell, a fungal cell, a yeast cell, a plant cell, or a eukaryotic cell line.

8. A process of producing a polypeptide with xylanase activity comprising culturing the host cell of claim 7 under conditions that provide for expression of the polypeptide.

9. A transgenic plant or part thereof comprising the polynucleotide of claim 1.

10. A transgenic plant or part thereof comprising the vector of claim 4.

11. An animal feed, food or foodstuff comprising the transgenic plant or part thereof of claim 9.

12. An animal feed, food or foodstuff comprising the transgenic plant or part thereof of claim 10.

* * * * *

SEQUENCE LISTING

<160> NUMBER OF SEQ ID NOS: 4

<210> SEQ ID NO 1
<211> LENGTH: 1227
<212> TYPE: DNA
<213> ORGANISM: Talaromyces emersonii
<220> FEATURE:
<221> NAME/KEY: CDS
<222> LOCATION: (1)..(1227)

<400> SEQUENCE: 1

```
atg gtt cgc ctc agt cca gtc ttg ctc gcc tcc atc gca ggc tct ggc      48
Met Val Arg Leu Ser Pro Val Leu Leu Ala Ser Ile Ala Gly Ser Gly
 1               5                  10                  15 ctg cct cta gcc caa gca gca ggc ctc aac aca gcc gcc aaa gcc atc      96
Leu Pro Leu Ala Gln Ala Ala Gly Leu Asn Thr Ala Ala Lys Ala Ile
             20                  25                  30 ggc ctg aaa tac ttt ggc aca gcg acc gac aac ccc gag ctg agc gac     144
Gly Leu Lys Tyr Phe Gly Thr Ala Thr Asp Asn Pro Glu Leu Ser Asp
         35                  40                  45 acc gcg tac gag acg cag ctc aac aac acg cag gat ttc ggg cag ttg     192
Thr Ala Tyr Glu Thr Gln Leu Asn Asn Thr Gln Asp Phe Gly Gln Leu
     50                  55                  60 acg ccg gcg aat tcg atg aag tgg gat gcc acc gag ccc gag cag aat     240
Thr Pro Ala Asn Ser Met Lys Trp Asp Ala Thr Glu Pro Glu Gln Asn
 65                  70                  75                  80 gtc ttc acg ttt agc gcc ggc gat cag att gcc aac ttg gcc aag gcg     288
Val Phe Thr Phe Ser Ala Gly Asp Gln Ile Ala Asn Leu Ala Lys Ala
                 85                  90                  95 aat ggc cag atg ttg cgg tgt cat aat ctt gtt tgg tac aat cag ttg     336
Asn Gly Gln Met Leu Arg Cys His Asn Leu Val Trp Tyr Asn Gln Leu
            100                 105                 110 ccg tcg tgg gtc acc agt ggc tcc tgg acc aac gag acg ctg ctt gct     384
Pro Ser Trp Val Thr Ser Gly Ser Trp Thr Asn Glu Thr Leu Leu Ala
        115                 120                 125 gcc atg aag aat cac atc acc aac gtc gtt acc cat tac aag ggc cag     432
Ala Met Lys Asn His Ile Thr Asn Val Val Thr His Tyr Lys Gly Gln
    130                 135                 140 tgc tac gca tgg gat gtc gtt aat gag gcc ctc aac gac gac ggc acc     480
Cys Tyr Ala Trp Asp Val Val Asn Glu Ala Leu Asn Asp Asp Gly Thr
145                 150                 155                 160 tac cgc agc aac gtc ttc tac cag tac atc ggt gag gcg tac atc ccc     528
Tyr Arg Ser Asn Val Phe Tyr Gln Tyr Ile Gly Glu Ala Tyr Ile Pro
                165                 170                 175
```

```
atc gcc ttc gcg acg gcc gcc gcc gcc gac ccc aac gcc aag ctg tac      576
Ile Ala Phe Ala Thr Ala Ala Ala Ala Asp Pro Asn Ala Lys Leu Tyr
            180                 185                 190 tac aac gac tac aac atc gag tac ccg ggg gcc aag gcg acg gcg gcg      624
Tyr Asn Asp Tyr Asn Ile Glu Tyr Pro Gly Ala Lys Ala Thr Ala Ala
        195                 200                 205 cag aac ctg gtc aag ctg gtg cag tcg tac ggc gcg cgc atc gac ggc      672
Gln Asn Leu Val Lys Leu Val Gln Ser Tyr Gly Ala Arg Ile Asp Gly
    210                 215                 220 gtc ggc ctg cag tcg cac ttc atc gtg ggc gag acg ccc agc acc agc      720
Val Gly Leu Gln Ser His Phe Ile Val Gly Glu Thr Pro Ser Thr Ser
225                 230                 235                 240 tcc cag cag cag aac atg gcc gcc ttc acg gcg ctg ggc gtc gag gtc      768
Ser Gln Gln Gln Asn Met Ala Ala Phe Thr Ala Leu Gly Val Glu Val
                245                 250                 255 gcc atc acc gag ctc gac atc cgc atg cag ctg ccc gag acg gaa gcc      816
Ala Ile Thr Glu Leu Asp Ile Arg Met Gln Leu Pro Glu Thr Glu Ala
            260                 265                 270 ctg ctg acg cag cag gcc acc gac tac cag agc acc gtg cag gcc tgc      864
Leu Leu Thr Gln Gln Ala Thr Asp Tyr Gln Ser Thr Val Gln Ala Cys
        275                 280                 285 gcc aac acc aag ggc tgc gtc ggc atc acc gtc tgg gac tgg acc gac      912
Ala Asn Thr Lys Gly Cys Val Gly Ile Thr Val Trp Asp Trp Thr Asp
    290                 295                 300 aag tac tcg tgg gtg ccc agc acc ttc tcg ggc tat ggc gac gcc tgt      960
Lys Tyr Ser Trp Val Pro Ser Thr Phe Ser Gly Tyr Gly Asp Ala Cys
305                 310                 315                 320 ccc tgg gac gcc aac tac cag aag aag ccc gcg tac gaa ggc atc ctc     1008
Pro Trp Asp Ala Asn Tyr Gln Lys Lys Pro Ala Tyr Glu Gly Ile Leu
                325                 330                 335 act ggg ctt gga cag acg gtc acc agc acc acc tac atc atc tcg ccg     1056
Thr Gly Leu Gly Gln Thr Val Thr Ser Thr Thr Tyr Ile Ile Ser Pro
            340                 345                 350 acg acg tct gtc gga acg ggc acg acc tcg agc gga gga agc ggc         1104
Thr Thr Ser Val Gly Thr Gly Thr Thr Thr Ser Ser Gly Gly Ser Gly
        355                 360                 365 ggc acg act ggc gtg gcc cag cat tgg gag cag tgc ggt gga ctg ggc     1152
Gly Thr Thr Gly Val Ala Gln His Trp Glu Gln Cys Gly Gly Leu Gly
    370                 375                 380 tgg act ggt ccg acg gtt tgc gca agt ggc tac act tgc act gtc atc     1200
Trp Thr Gly Pro Thr Val Cys Ala Ser Gly Tyr Thr Cys Thr Val Ile
385                 390                 395                 400 aat gag tat tac tcg cag tgt ctg taa                                 1227
Asn Glu Tyr Tyr Ser Gln Cys Leu
                405

<210> SEQ ID NO 2
<211> LENGTH: 408
<212> TYPE: PRT
<213> ORGANISM: Talaromyces emersonii

<400> SEQUENCE: 2

Met Val Arg Leu Ser Pro Val Leu Leu Ala Ser Ile Ala Gly Ser Gly
 1               5                  10                  15

Leu Pro Leu Ala Gln Ala Ala Gly Leu Asn Thr Ala Ala Lys Ala Ile
            20                  25                  30

Gly Leu Lys Tyr Phe Gly Thr Ala Thr Asp Asn Pro Glu Leu Ser Asp
        35                  40                  45

Thr Ala Tyr Glu Thr Gln Leu Asn Asn Thr Gln Asp Phe Gly Gln Leu
    50                  55                  60
```

Thr Pro Ala Asn Ser Met Lys Trp Asp Ala Thr Glu Pro Glu Gln Asn
 65                  70                  75                  80

Val Phe Thr Phe Ser Ala Gly Asp Gln Ile Ala Asn Leu Ala Lys Ala
                 85                  90                  95

Asn Gly Gln Met Leu Arg Cys His Asn Leu Val Trp Tyr Asn Gln Leu
            100                 105                 110

Pro Ser Trp Val Thr Ser Gly Ser Trp Thr Asn Glu Thr Leu Leu Ala
        115                 120                 125

Ala Met Lys Asn His Ile Thr Asn Val Val Thr His Tyr Lys Gly Gln
130                 135                 140

Cys Tyr Ala Trp Asp Val Val Asn Glu Ala Leu Asn Asp Asp Gly Thr
145                 150                 155                 160

Tyr Arg Ser Asn Val Phe Tyr Gln Tyr Ile Gly Glu Ala Tyr Ile Pro
                165                 170                 175

Ile Ala Phe Ala Thr Ala Ala Ala Asp Pro Asn Ala Lys Leu Tyr
            180                 185                 190

Tyr Asn Asp Tyr Asn Ile Glu Tyr Pro Gly Ala Lys Ala Thr Ala Ala
            195                 200                 205

Gln Asn Leu Val Lys Leu Val Gln Ser Tyr Gly Ala Arg Ile Asp Gly
210                 215                 220

Val Gly Leu Gln Ser His Phe Ile Val Gly Glu Thr Pro Ser Thr Ser
225                 230                 235                 240

Ser Gln Gln Gln Asn Met Ala Ala Phe Thr Ala Leu Gly Val Glu Val
                245                 250                 255

Ala Ile Thr Glu Leu Asp Ile Arg Met Gln Leu Pro Glu Thr Glu Ala
            260                 265                 270

Leu Leu Thr Gln Gln Ala Thr Asp Tyr Gln Ser Thr Val Gln Ala Cys
            275                 280                 285

Ala Asn Thr Lys Gly Cys Val Gly Ile Thr Val Trp Asp Trp Thr Asp
290                 295                 300

Lys Tyr Ser Trp Val Pro Ser Thr Phe Ser Gly Tyr Gly Asp Ala Cys
305                 310                 315                 320

Pro Trp Asp Ala Asn Tyr Gln Lys Lys Pro Ala Tyr Glu Gly Ile Leu
                325                 330                 335

Thr Gly Leu Gly Gln Thr Val Thr Ser Thr Thr Tyr Ile Ile Ser Pro
            340                 345                 350

Thr Thr Ser Val Gly Thr Gly Thr Thr Ser Gly Gly Ser Gly
            355                 360                 365

Gly Thr Thr Gly Val Ala Gln His Trp Glu Gln Cys Gly Gly Leu Gly
370                 375                 380

Trp Thr Gly Pro Thr Val Cys Ala Ser Gly Tyr Thr Cys Thr Val Ile
385                 390                 395                 400

Asn Glu Tyr Tyr Ser Gln Cys Leu
                405

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: primer #1

<400> SEQUENCE: 3
tatagcgaaa tggattgatt gtacgctc                                    28

```
<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: primer #2

<400> SEQUENCE: 4
atccccagca tcattacacc tcagtg                                          26
```